(12) United States Patent
Wyse et al.

(10) Patent No.: US 9,289,425 B2
(45) Date of Patent: Mar. 22, 2016

(54) INTRANASAL NALOXONE COMPOSITIONS AND METHODS OF MAKING AND USING SAME

(71) Applicant: AntiOp, Inc., Lexington, KY (US)

(72) Inventors: Joseph Wyse, Nicholasville, KY (US); Michael Paul DeHart, Winterville, NC (US)

(73) Assignee: AntiOp, Inc., Lexington, KY (US)

( * ) Notice: Subject to any disclaimer, the term of this patent is extended or adjusted under 35 U.S.C. 154(b) by 0 days.

(21) Appl. No.: 14/882,857

(22) Filed: Oct. 14, 2015

(65) Prior Publication Data

US 2016/0038480 A1    Feb. 11, 2016

Related U.S. Application Data

(63) Continuation of application No. 14/576,357, filed on Dec. 19, 2014, now Pat. No. 9,192,570.

(60) Provisional application No. 61/918,802, filed on Dec. 20, 2013.

(51) Int. Cl.
| | |
|---|---|
| *A61K 31/70* | (2006.01) |
| *A61K 31/485* | (2006.01) |
| *A61K 9/00* | (2006.01) |
| *A61K 47/12* | (2006.01) |
| *A61K 47/18* | (2006.01) |
| *A61K 47/10* | (2006.01) |

(52) U.S. Cl.
CPC ............. *A61K 31/485* (2013.01); *A61K 9/0043* (2013.01); *A61K 47/10* (2013.01); *A61K 47/12* (2013.01); *A61K 47/183* (2013.01)

(58) Field of Classification Search
USPC ......................................................... 514/23
See application file for complete search history.

(56) References Cited

U.S. PATENT DOCUMENTS

| | | | |
|---|---|---|---|
| 4,181,726 A | 1/1980 | Bernstein | |
| 4,464,378 A | 8/1984 | Hussain | |
| 5,482,965 A | 1/1996 | Rajadhyaksha | |
| 5,622,657 A | 4/1997 | Takada et al. | |
| 5,733,572 A | 3/1998 | Unger et al. | |
| 5,866,154 A | 2/1999 | Bahal et al. | |
| 5,908,825 A | 6/1999 | Fasano et al. | |
| 5,958,962 A | 9/1999 | Cook | |
| 6,284,765 B1 | 9/2001 | Caffrey | |
| 6,359,111 B1 | 3/2002 | Meyer et al. | |
| 6,436,950 B1 | 8/2002 | Achari et al. | |
| 6,716,449 B2 | 4/2004 | Oshlack et al. | |
| 6,776,978 B2 | 8/2004 | Rabinowitz et al. | |
| 6,969,508 B2 | 11/2005 | Duggar | |
| 7,078,018 B2 | 7/2006 | Rabinowitz et al. | |
| 7,090,830 B2 | 8/2006 | Hale et al. | |
| 7,501,434 B2 | 3/2009 | Shah et al. | |
| 7,563,899 B2 | 7/2009 | Boyd et al. | |
| 7,745,665 B2 | 6/2010 | Gant et al. | |
| 7,872,013 B2 | 1/2011 | Gant et al. | |
| 7,910,599 B2 | 3/2011 | Sinclair | |
| 7,915,285 B2 | 3/2011 | Johnson et al. | |
| 7,964,183 B2 | 6/2011 | Eliaz et al. | |
| 8,034,825 B2 | 10/2011 | Bentley et al. | |
| 8,063,059 B2 | 11/2011 | Hermann | |
| 8,247,425 B2 | 8/2012 | Bazhina et al. | |
| 8,263,618 B2 | 9/2012 | Long et al. | |
| 8,337,817 B2 | 12/2012 | Nagata et al. | |
| 8,343,992 B2 | 1/2013 | Doshan et al. | |
| 8,383,129 B2 | 2/2013 | Gonzalez-Mariscal et al. | |
| 8,512,727 B2 | 8/2013 | Cooper et al. | |
| 8,530,463 B2 | 9/2013 | Cartt et al. | |
| 8,627,816 B2 | 1/2014 | Edwards et al. | |
| 8,710,069 B2 | 4/2014 | Holtman et al. | |
| 8,710,070 B2 | 4/2014 | Holtman et al. | |
| 8,784,872 B2 | 7/2014 | Oronsky et al. | |
| 8,889,635 B2 | 11/2014 | Baker, Jr. et al. | |
| 8,992,974 B2 | 3/2015 | McCarty | |
| 9,005,626 B2 | 4/2015 | Seigfried | |
| 9,101,539 B2 | 8/2015 | Nagata et al. | |
| 9,101,540 B2 | 8/2015 | Hovey et al. | |
| 9,192,570 B2 * | 11/2015 | Wyse ................... | A61K 9/0043 |
| 2003/0077300 A1 | 4/2003 | Wermeling | |
| 2003/0191147 A1 | 10/2003 | Sherman et al. | |
| 2004/0102440 A1 | 5/2004 | Wong | |
| 2004/0105881 A1 | 6/2004 | Cevc et al. | |

(Continued)

FOREIGN PATENT DOCUMENTS

| | | |
|---|---|---|
| CN | 1 575 795 A | 2/2005 |
| CN | 1 726 915 A | 2/2006 |
| CN | 101036651 A | 9/2007 |
| EP | 0 880 352 B1 | 2/1998 |
| EP | 1 810 670 A1 | 7/2007 |
| EP | 2 266 563 | 12/2010 |
| RU | 2 344 822 | 1/2009 |
| WO | WO 82/03768 | 11/1982 |
| WO | WO 93/24164 | 12/1993 |

(Continued)

OTHER PUBLICATIONS

Albert, S., et al., "Project Lazarus: Community-Based Overdose Prevention in Rural North Carolina", Pain Medicine, 2011, 12:S77-S85.

(Continued)

*Primary Examiner* — Rei-Tsang Shiao

(74) *Attorney, Agent, or Firm* — Frost Brown Todd LLC

(57) ABSTRACT

Disclosed herein are compositions containing an opioid antagonist such as naloxone and one or more pharmaceutically acceptable excipients. The compositions may be used for intranasal delivery of Naloxone for the treatment of, for example, opioid overdose in an individual in need thereof. Also disclosed are methods of making compositions containing Naloxone, and devices for nasal delivery of naloxone compositions.

10 Claims, 5 Drawing Sheets

(56) References Cited

U.S. PATENT DOCUMENTS

| | | |
|---|---|---|
| 2004/0142959 A1 | 7/2004 | Jackson |
| 2004/0167146 A1 | 8/2004 | Jackson |
| 2004/0180916 A1 | 9/2004 | Levine |
| 2005/0038062 A1 | 2/2005 | Burns et al. |
| 2005/0126562 A1 | 6/2005 | Rabinowitz et al. |
| 2005/0214223 A1 | 9/2005 | Bartholomaeus et al. |
| 2005/0222135 A1 | 10/2005 | Buschmann et al. |
| 2005/0233001 A1 | 10/2005 | Hovey et al. |
| 2005/0245483 A1 | 11/2005 | Brogmann et al. |
| 2005/0245556 A1 | 11/2005 | Brogmann et al. |
| 2006/0009478 A1 | 1/2006 | Friedmann et al. |
| 2006/0110333 A1 | 5/2006 | Yanagawa |
| 2006/0111382 A1 | 5/2006 | Shafer et al. |
| 2006/0120962 A1 | 6/2006 | Rabinowitz et al. |
| 2006/0120967 A1 | 6/2006 | Namburi et al. |
| 2007/0082893 A1 | 4/2007 | Buschmann et al. |
| 2007/0212307 A1 | 9/2007 | Wermeling et al. |
| 2008/0026052 A1 | 1/2008 | Schoenhard |
| 2008/0066741 A1 | 3/2008 | LeMahieu et al. |
| 2008/0078382 A1 | 4/2008 | LeMahieu et al. |
| 2008/0145429 A1 | 6/2008 | Leyendecker et al. |
| 2008/0146549 A1 | 6/2008 | Coleman |
| 2008/0152595 A1 | 6/2008 | Emigh et al. |
| 2008/0171762 A1 | 7/2008 | Ockert |
| 2008/0176884 A1 | 7/2008 | Perez et al. |
| 2008/0207669 A1 | 8/2008 | Perez et al. |
| 2008/0234306 A1 | 9/2008 | Perez et al. |
| 2009/0041687 A1 | 2/2009 | Beumer et al. |
| 2009/0041800 A1 | 2/2009 | Woiwode et al. |
| 2009/0047279 A1 | 2/2009 | Perez et al. |
| 2009/0111741 A1 | 4/2009 | Aldrich et al. |
| 2009/0246256 A1 | 10/2009 | Al-Ghananeem |
| 2009/0297611 A1 | 12/2009 | Robinson et al. |
| 2010/0041689 A1 | 2/2010 | Johnson et al. |
| 2010/0087337 A1 | 4/2010 | Dewitt |
| 2010/0143449 A1 | 6/2010 | Kolesnikov |
| 2010/0144645 A1 | 6/2010 | Kirk et al. |
| 2010/0168147 A1 | 7/2010 | Chapleo et al. |
| 2010/0221339 A1 | 9/2010 | Hermann |
| 2010/0222257 A1 | 9/2010 | Gant et al. |
| 2010/0226989 A1 | 9/2010 | Hovey et al. |
| 2010/0286186 A1 | 11/2010 | Franklin et al. |
| 2010/0294268 A1 | 11/2010 | Wensley et al. |
| 2010/0311691 A1 | 12/2010 | Barkan et al. |
| 2010/0331354 A1 | 12/2010 | Wermeling |
| 2011/0065628 A1 | 3/2011 | Johnson et al. |
| 2011/0105551 A1 | 5/2011 | Birch et al. |
| 2012/0040009 A1 | 2/2012 | Hermann |
| 2012/0270895 A1 | 10/2012 | Wermeling |
| 2013/0059876 A1 | 3/2013 | Angeli et al. |
| 2014/0171458 A1 | 6/2014 | Brown et al. |
| 2015/0174061 A1 | 6/2015 | Wyse et al. |
| 2015/0258019 A1 | 9/2015 | Crystal et al. |

FOREIGN PATENT DOCUMENTS

| | | |
|---|---|---|
| WO | WO 98/30211 | 7/1998 |
| WO | WO 99/11250 | 3/1999 |
| WO | WO 00/62757 | 10/2000 |
| WO | WO 00/74652 | 12/2000 |
| WO | WO 2005/020906 | 3/2005 |
| WO | WO 2008/139170 | 11/2008 |
| WO | WO 2009/040595 | 4/2009 |
| WO | WO 2009/049233 | 4/2009 |
| WO | WO 2011/144746 | 11/2011 |
| WO | WO 2012/156317 | 11/2012 |

OTHER PUBLICATIONS

Alexander, MD, J. L., et al., "Suspected Opioid-Related Emergency Medical Services Encounters in a Rural State, 1997-2002", Prehospital Emergency Care, Oct./Dec. 2004, vol. 8, No. 4, pp. 427-430.

Anonymous: "Narcan", Drugs.com, print version, Jan. 1, 2006, www.drugs.com/pro/narcan.html?printedable=1, retrieved Feb. 19, 2015.

Ashworth, A.J., et al., "Take home naloxone for opiate addicts: Apparent advantages may be balanced by hidden harms", BMJ, vol. 323, Oct. 20, 2001, p. 935.

Aurora, MD, J. "Development of Nasal Delivery Systems: A Review", Drug Development & Delivery, Oct. 2002, vol. 2, No. 7, 5 pgs.

Barton, MD, E.D., et al., "Efficacy of Intranasal Naloxone as a Needless Alternative for Treatment of Opioid Overdose in the Prehospital Setting", The Journal of Emergency Medicine, vol. 29, No. 3, pp. 265-271, 2005.

Barton, MD, MS; E.D. et al., "Intranasal Administration of Naloxone by Paramedics", Prehospital Emergency Care , Jan./Mar. 2002;6(1):54-8.

Baumann, MD, B.M., et al., "Use and efficacy of nebulized naloxone in patients with suspected opioid intoxication", American Journal of Emergency Medicine, vol. 31, 2013, pp. 585-588.

Behl, C.R., et al., "Effect of physicochemical properties and other factors on systemic nasal drug delivery", Advanced Drug Delivery Reviews, 1998, 29:89-116, 28 pgs.

Beletsky, L., et al., "Physicians' Knowledge of and Willingness to Prescribe Naloxone to Reverse Accidental Opiate Overdose: Challenges and Opportunities", Journal of Urban Health: Bulletin of the New York Academy of Medicine, vol. 84, No. 1, 2006, pp. 126-136.

Beletsky, L., et al., Closing Death's Door: Action Steps to Facilitate Emergency Opioid Drug Overdose Reversal in the United States A Conference Report from The Center for Health Law, Politics and Policy Temple University Beasley School of Law, 2009.

Belz, BA, D., et al., "Naloxone Use in a Tiered-Response Emergency Medical Services System", Prehospital Emergency Care, Oct.-Dec. 2006: 10, 4, pp. 468-471.

Berstein, J.A., et al., "Double-blind placebo-controlled trial of reformulated azelastine nasal spray in pateints with seasonal allergic rhinitis", Am J Rhinol Allergy, 2009, vol. 23, pp. 512-517. Abstract only.

Blackwood, G., "Take home naloxone for opiate addicts: Figures in Jersey give no Isupport to scheme's effectiveness", BMJ, vol. 323, Oct. 20, 2001, pp. 934-935.

Bohnert, Asb, et al., "Association Between Opioid Prescribing Patterns and Opioid Overdose-Related Deaths", JAMA, 2011, 305(13):1315-1321.

Boyd, J.J., et al., "Recurrent opioid toxicity after pre-hospital care of presumed heroin overdose patients", Acta Anaesthesiol Scand, 2006; 50:1266-1270.

Bracken, M.B., et al., "A Randomized, Controlled Trial of Methylprednisolone or Naloxone in the Treatnmet of Acute Spina-Cord Injury—Results of the Second National Acute Spinal Court Injury Study", N Engl J Med, 2009, 322:1405-1411.

Bristol-Myers Squibb. Butorphanol tartrate nasal spray prescribing information 2002, 11 pgs.

Buajordet, I., et al., "Adverse events after naloxone treatment of episodes of suspected acute opioid overdose", European Journal of Emergency Medicine, 2004, vol. 11, No. 1, p. 19-23.

Burris, S., et al., "Legal Aspects of Providing Naloxone to Heroin users in the United States", International Journal of Drug Policy, 2001; 12:237-248.

Burris, S. et al., "Stopping an Invisible epidemic: Legal Issues in the Provision of Naloxone to Prevent Opioid Overdose", Drexel Law Review, 2009, 1(2):273-339.

Cantwell, K., et al., "The relationship between naloxone dose and key patient variables in the treatment of non-fatal heroin overdose in the prehospital setting", Resuscitation, 2005, vol. 65, pp. 315-319.

Centers for Disease Control and Prevention, "Emergency department visits involving nonmedical use of selected prescription drugs—United States, 2004-2008", MMWR Morbidity and mortality weekly report 2010;59(23):705-9.

Centers for Disease Control and Prevention, Morbidity and Mortality Weekly Report. Vital signs: overdoses of prescription opioid pain relievers—United States, 1999-2008. Nov. 4, 2011; 60(43):1487-1492.

Centers for Disease Control and Prevention, National Center for Health Statistics. Deaths: preliminary data for 2009, Natl Vital Stat Rep., 2011; 59:17-20.

(56) References Cited

OTHER PUBLICATIONS

City and County of San Francisco, Department of Public Health, "Naloxone Training for providers", Nov. 8, 2012., pp. 1-9.
Clark, et al, "A Systematic Review of Community Opioid Overdose Prevention and Naloxone Distribution Programs" J Addict Med, May/Jun. 2014, vol. 8, No. 3, pp. 153-163.
Clark, SFJ, et al., "Naloxone in Opioid Poisoning: Walking the Tightrope", Emerg Med J 2005, 222:612-616.
Coda, MD, B.A., et al., "Pharmacokinetics and Bioavailability of Single-Dose Intranasal Hydromorphone Hydrochloride in Healthy Volunteers", Anesth Analg. 2003; 97:117-23.
Compton, MD, MPE, W.M., et al., "Expanded Access to Opioid Overdose Intervention: Research, Practice, and Policy Needs", Annals of Internal Medicine, Jan. 1, 2013, vol. 158, No. 1, pp. 65-66.
Costantino, H..R, et al. "Intranasal delivery: Physicochemical and therapeutic aspects", Int J Pharm, 2007; 337:1-24.
Dale, O., et al., "Nasal administration of opioids for pain management in adults", Acta Anaesthesiol Scand. 2002; 46:759-70.
Doe-Simkins, M., et al., "Saved by the Nose: Bystander-Administered Intranasal Naloxone Hydrochloride for Opioid Overdose", American Journal of Public Health, May 2009, vol. 99, No. 5, pp. 788-791.
Dowling, et al, "Population Pharmacokinetics of Intravenous, Intramuscular, and Intranasal Naloxone in Human Volunteers," Therapeutic Drug Monitoring, 30(4):490-496 (2008).
Drug Abuse Warning Network, The DAWN Report, Highlights of the 2010 Drug Abuse Warning Network (DAWN) Findings on Drug-Related Emergency Department Visits, Jul. 2, 2012, pp. 1-8.
European Directorate for the Quality of Medicines & Healthcare, European Pharmacopoeia (Ph. Eur.), CRS Information Leaflet, Ph. Eur. Reference Standard, *Naloxone Hydrochloride Dihydrate CRS batch* 2 (EP catalog code N0075000), Sep. 22, 2014, 2 pgs.
European Directorate for the Quality of Medicines & Healthcare, European Pharmacopoeia (Ph. Eur.), Ph. Eur. Reference Standard—LEAFLET, *Naloxone for Peak Identification CRS batch* 1 (EP catalog code Y0000695), Oct. 30, 2008, 2 pgs.
FDA Draft Guidance for Industry and Food and Drug Administration Staff—Applying Human Factors and Usability Engineering to Optimize Medical Device, Jun. 22, 2011, pp. 1-37.
FDA Guidance for Industry, "Nasal Spray and Inhalation Solution, Suspension, and Spray Drug Products—Chemistry Manufacturing, and Controls Documentation", Jul. 2002, pp. 1-49.
Fernandez, MD, MPH, W., et al., "Trends in opioid-related fatal overdoses in Massachusetts, 1990-2003", J Subst Abuse Treat. 2006; 31:151-6.
Flamm, E.S., et al., "A Phase I trial of naloxone treatment in acute spinal cord injury", Journal of Neurosurgery, Sep. 1985, vol. 63, No. 3, pp. 390-397.
Gaston, R. L., et al., "Can we prevent drug related deaths by training opioid users to recognise and manage overdoses?", Harm Reduction Journal, 2009, 6:26, 35 pgs.
Graham, C.A., et al. "Take home naloxone for opiate addicts: Drug misusers may benefit from training in cardiopulmonary resuscitation", BMJ, vol. 323, Oct. 20, 2001, p. 934.
Hall, DVM, MSPH, A.J., et al., "Patterns of Abuse Among Unintentional Pharmaceutical Overdose Fatalities", JAMA, Dec. 10, 2008, vol. 300, No. 22, pp. 2613-2620.
Havens, J.R., et al., "Prevalence of opioid analgesic injection among rural nonmedical opioid analgesic users", Drug Alcohol Depend. 2007; 87:98-102.
Heard, MD, C., et al., "Case report: Intranasal flumazenial and naloxone to reverse over-sedation in a child undergoing dental restorations", Pediatric Anesthesia, 2009, vol. 19, pp. 795-799.
Hewlett, PharmD, L., et al., "Survey of naloxone legal status in opioid overdose prevention and treatment", Journal of Opioid Management, Sep./Oct. 2013, vol. 5, No. 5, pp. 369-377.
Hospira, Inc. Naloxone hydrochloride injection package insert. 2007.
Hospira, Inc., Naloxone Hydrochloride injection solution, prescribing information, Nov. 2006.

Hussain, A., et al., "Nasal absorption of naloxone and buprenorphine in rats", Int Journal Pharm, Sep. 1984, vol. 21, Issue 2, pp. 233-237.
International Medication Systems L. Naloxone hydrochloride injection package insert. 2006.
International Medication Systems, Limited, Naloxone Hydrochloride—naloxone hydrochloride injection, prescribing information, Aug. 2001.
Intranasal drug delivery—General Principles, date unknown, 2 pgs. [Please treat as prior art until proven otherwise].
Jones, C.M. et al., "Pharmaceutical Overdose Deaths, United States, 2010", JAMA 2013;309:657-9.
Kelly, A-M., "Intranasal naloxone for life threatening opioid toxicity", Emergency Medicine Journal, 2002; 19:14, 375.
Kelly, A-M., et al., "Randomised trial of intranasal versus intramuscular naloxone in prehospital treatment for suspected opioid overdose", MJA, Jan. 3, 2005, vol. 182, No. 1, pp. 24-27.
Kentucky Science and Technology Corporation (KSTC), Grant Agreement No. KSTC-184-512-11-104, Naloxone Nasal Spray Administration, Patent and Business Plan Development, Alcomed, Inc., Feb. 1, 2011-Jan. 31, 2012, 16 pgs.
Kentucky Science and Technology Corporation (KSTC), Grant Agreement No. KSTC-184-512-12-125, Naloxone Nasal Spray Development, Alcomed, Inc., Apr. 1, 2012-Mar. 31, 2013, 17 pgs.
Kerr, D., et al., "Intranasal naloxone for the treatment of suspected heroin overdose", Addition, 2008, vol. 103, pp. 379-386.
Kerr, D., et al., "Randomized controlled trial comparing the effectiveness and safety of intranasal and intramuscular naloxone for the treatment of suspected heroin overdose", Addition, 2009, vol. 104, pp. 2067-2074.
Kim, MPH, D., et al., "Expanded Access to Naloxone: Options for Critical Response to the Epidemic of Opioid Overdose Mortality", American Journal of Public Health, Mar. 2009, vol. 99, No. 3, pp. 402-407.
Loimer, M.D., N., et al., "Nasal Administration of Naloxone Is as Effective as the Intravenous Route in Opiate Addicts", The International Journal of the Addictions, 1994, vol. 29, No. 6, pp. 819-827.
Loimer, N., et al., "Nasal Administration of Naloxone for Detection of Opiate Dependence", J. Psychiat. Res., 1992, vol. 26, No. 1, pp. 39-43.
Mack, PhD, K.A., et al., "Vital Signs: Overdoses of Prescription Opioid Pain Relievers and Other Drugs Among Women—United States, 1999-2010", Centers for Disease Control and Prevention, Morbidity and Mortality Weekly Report, Early Release/vol. 62, Jul. 2, 2013.
Manchikanti, MD, L. et al., "Therapeutic Use Abuse, and Nonmedical Use of Opioids: a Ten-Year Perspective", Pain Phys. 2010; 13:401-35.
Marx, J., Ed. et al., Rosen's Emergency Medicine. 7th ed. St. Louis, MO; 2010.
Merlin, Do, EMT-P, M.A. et al., "Intranasal naloxone delivery is an alternative to intravenous naloxone for opioid overdoses", American Journal of Emergency Medicine, 2010, vol. 28, pp. 296-303.
Middleton, L.S., et al., "The pharmacodynamic and pharmacokinetic profile of intranasal crushed buprenorphine and buprenorphine/naloxone tablets in opioid abusers", Addiction, 2011, vol. 106, pp. 1460-1473.
Mountain, D. "Take home naloxone for opiate addicts: Big conclusions are drawn from little evidence", BMJ, vol. 323, Oct. 20, 2001, p. 934.
Ngai, MD, S.H., et al., "Pharmacokinetics of Naloxone in Rats and in Man: Basis for its Potency and Short Duration of Action", Anesthesiology, 1976; 44:398-401.
Osterwalder, MD, MPH, J.J. "Naloxone—for Intoxications with Intravenous Heroin and Heroin Mixtures—Harmless of Hazardous? A Prospective Clinical Study", Clin Toxicol. 1996; 34:409-16.
Paulozzi, L., et al., "Prescription drug laws, drug overdoses, and drug sales in New York and Pennsylvania", Journal of Public Health Policy, 2010, vol. 31, No. 4, pp. 422-432.
Paulozzi, L.J. et al., "US data show sharply rising drug-induced death rates", Injury prevention : journal of the International Society for Child and Adolescent Injury Prevention, 2007;13:130-2.
Paulozzi, MD, L.J., "Vital Signs: Variation Among States in Prescribing of Opioid Pain Relievers and Benzodiazepines—United States,

(56) References Cited

OTHER PUBLICATIONS

2012", Centers for Disease Control and Prevention, Morbidity and Mortality Weekly Report, Early Release/vol. 63, Jul. 1, 2014.
Piper, T.M., et al., "Overdose prevention for injection drug users: Lessons learned from naloxone training and distribution programs in New York City", Harm Reduction Journal, 2007;4:3, 8 pgs.
Pires, A., et al., "Intranasal Drug Delivery: How, Why and What for?", J Pharm Pharmaceut Sci, 12(3):288-311, 2009, 24 pgs.
Prescribe to Prevent: Prescribe Naloxone, Save a Life. (Accessed Jan. 1, 2013, at http://www.prescribetoprevent.org/.) pp. 1-16.
Project Lazarus: Community-based Overdose Prevention from North Carolina and the Community Care Chronica Pain Initiative, Available at http://projectlazarus.org/ , Accessed Jul. 19, 2012, pp. 1-42.
Richardson, MD, J., "Lexington—Fayette Urban County Government Division of Fire & Emergency Services", Jul. 1, 2007.
Robertson, T.M., et al., "Intranasal Naloxone is a Viable Alternative to Intravenous Naloxone for Prehospital Narcotic Overdose", Prehospital emergency care : official journal of the National Association of EMS Physicians and the National Association of State EMS Directors 2009;13:512-5.
Rudy, PhD, A.C., et al., "A Multiple-Dose Phase I Study of Intranasal Hydromorphone Hydrochloride in Healthly Volunteers", Ambulatory Anesthesia, 2004: 99:1379-86.
Seal, K.H., et al., "Naloxone Distribution and Cardiopulmonary Resuscitation Training for Injection Drug Users to Prevent Heroin Overdose Death: A Pilot Intervention Study", J Urban Health, Jun. 2005, 82(2):303-311.
Seal, K.H., et al., "Predictors and Prevention of Nonfatal Overdose Among Street-Recruited Injection Heroin Users in the San Francisco Bay Area, 1998-1999", American Journal of Public Health 2001; 91:1842-6.
Seigler, A. et al, "Unintentional opioid overdose deaths in New York City, 2005-2010: A place-based approach to reduce risk", International Journal of Drug Policy, May 2014;25(3):569-74.
Shah, N.G., et al., "Unintentional drug overdose death trends in New Mexico, USA, 1990-2005: combinations of heroin, cocaine, prescription opioids and alcohol", Addiction. 2007; 103:126-36.
Sherman, S.G. et al. "The life they save may be mine : Diffusion of overdose prevention information from a city sponsored programme", International Journal of Drug Policy, 2009; 20:137-42.
Sporer, K.A., et al., "Out-of-hospital Treatment of Opioid Overdoses in an Urban Setting", Academic Emergency Medicine, Jul. 1996, vol. 3, No. 7, 660-7.
Sporer, K.A. et al., "Prescription Naloxone: A Novel Approach to Heroin Overdose Prevention", Annals of Emergency Medicine, Feb. 2007; vol. 49, No. 2, pp. 172-177.
Strang, J., "Take home naloxone for opiate addicts: Author's reply", BMJ, vol. 323, Oct. 20, 2001, p. 935.
Vilke GM, et al., "Are heroin overdose deaths related to patient release after prehospital treatment with naloxone?", Prehosp Emerg Care. 1999; 3:183-6.
Vilke, MD, G.M., et al., "Assessment for Deaths in Out-of-hospital Heroin Overdose Patients Treated with Naloxone Who Refuse Transport", Acad Emerg Med. 2003; 10:893-6.

Walley, A.Y., et al., "Opioid overdose rates and implementation of overdose education and nasal naloxone distribution in Massachusetts: interrupted time series analysis", BMJ, 2013; 346:f174.
Wallhäußer, K.H., "Die mikrobielle Kontamination von Kosmetika Rohstoffe—Produktion—Konservierung", Parfümerie und Kosmetik, 53. Jahrgang, Nr. Nov. 1972. German Language only.
Wanger, K., et al., "Intravenous vs subcutaneous naloxone for out-of-hospital management of presumed opioid overdose", Academic emergency medicine : official journal of the Society for Academic Emergency Medicine, 1998;5:293-9.
Warner, M., et al., "Drug poisoning deaths in the United States, 1980-2008", NCHS data brief, No. 81. Hyattsville, MD: National Center for Health Statistics. 2011.
Warner, PhD, M, et al., "Increase in fatal poisonings involving opioid analgesics in the United States, 1999-2006", NCHS data brief, 2009:1-8.
Warner, PhD, M., et al., "Trends in Drug-poisoning Deaths Involving Opioid Analgesics and Heroin: United States, 1999-2012", NCHS data brief, Dec. 2014.
Wermeling, D.P., "A response to the opioid overdose epidemic: naloxone nasal spray", Drug Deliv. and Transl. Res., Aug. 1, 2012.
Wermeling, D.P., "Opioid Harm Reduction Strategies: Focus on Expanded Access to Intranasal Naloxone", Pharmacotherapy, 2010; 30(7):627-31.
Wermeling, D.P., et al., "A Multicenter, Open-Label, Exploratory Dose-Ranging Trial of Intranasal Hydromorphone for Managing Acute Pain from Traumatic Injury", J Pain. 2010; 11:24-31.
Wermeling, PharmD, D.P. et al., "Pharmacokinetics, Bioequivalence, and Spray Weight Reproducibility of Intranasal Butorphanol After Administration With 2 Different Nasal Spray Pumps", J Clin Pharmacol. 2005; 45:969-73.
Wheeler, E, et al., "Community-Based Opioid Overdose Prevention Programs Providing Nalozone—United States, 2010", Centers for Disease Control and Prevention, Morbidity and Mortality Weekly Report, vol. 61, No. 6, Feb. 17, 2012, pp. 101-105.
Yealy, D.M. et al., "The Safety of Prehospital Naloxone Administration by Paramedics", Ann Emerg Med., Aug. 1990, vol. 19, No. 8, pp. 902-905.
Yokell, ScB, M.A., et al., "Opioid Overdose Prevention and Naloxone Distribution in Rhode Island", Med Health R.I., Aug. 2011; 94(8):240-242.
Yokell, ScB, M.A. et al., "Presentation of Prescription and Nonprescription Opioid Overdoses to US Emergency Departments", JAMA Internal Medicine, Oct. 27, 2014.
US Office Action dated Feb. 12, 2015 for U.S. Appl. No. 13/494,882, 8 pgs.
International Search Report dated Mar. 20, 2013 for Application No. PCT/EP2012/058792.
International Preliminary Report on Patentability and Written Opinion dated Nov. 19, 2013 for Application No. PCT/EP2012/058792.
International Search Report and Written Opinion dated Mar. 11, 2015 for Application No. PCT/US2014/071371.

* cited by examiner

INTRANASAL NALOXONE COMPOSITIONS AND METHODS OF MAKING AND USING SAME

CROSS-REFERENCE TO RELATED APPLICATIONS

This application is a continuation of and claims priority to and benefit of U.S. application Ser. No. 14/576,357, filed Dec. 19, 2014, which claims priority to and benefit of U.S. Provisional Application Ser. No. 61/918,802, filed Dec. 20, 2013, both of which are incorporated herein by reference in their entirety for all purposes.

TECHNICAL FIELD

The instant invention relates to compositions comprising an opioid antagonist, and methods and devices for using same.

BACKGROUND

Naloxone was approved by FDA in 1971 and first marketed as Narcan® injection for the complete or partial reversal of opioid intoxication. It has subsequently become a multi-source prescription generic drug and is currently manufactured by International Medication Systems, Limited (IMS) and Hospira, Inc. The injection is available in two strengths, 0.4 mg/mL and 1.0 mg/mL. Naloxone injection is approved worldwide and is on the WHO Model list of Essential Medicines as a specific antidote.

Presently, naloxone is a standard inventory item for emergency services personnel to carry in ambulances and medication kits for reversal of suspected opioid overdose in the pre-hospital setting. Hospital emergency departments also use this medication routinely for this purpose. The initial parenteral dose of naloxone for adults with known or suspected narcotic overdose is 0.4 to 2 mg, which may be repeated as needed to a total dose of 10 mg. The currently available formulations of naloxone are approved for intravenous (IV), intramuscular (IM) and subcutaneous (SC) administration. Naloxone is also indicated as a reversal agent when the effects of therapeutic use of opioids are no longer medically necessary, such as in reversal of opioid effects in general anesthesia.

In 2008, poisoning surpassed motor vehicle accidents as the leading cause of "injury deaths" in the United States (Warner 2011). Nearly 90% of poisoning deaths are caused by drugs. During the past 3 decades, the number of drug poisoning deaths increased six-fold from about 6,100 in 1980 to 36,500 in 2008. Of the 36,500 drug poisoning deaths in 2008, 14,800 involved prescription opioid analgesics. Approximately 3,000 deaths also involved heroin overdose (Warner 2011).

In emergency situations, it is known that the onset of action of the IV injection will be faster, so is preferred. Narcan® is a commercially available intravenous formulation of naloxone HCl that is administered to unresponsive opioid users who have overdosed. The shortcomings of this formulation and route of administration are 1) it takes time to establish IV access and this is exacerbated in individuals who have poor veins from frequent injections with dirty needles; 2) that those who are administering the drug are putting themselves at risk from needle-stick injury from an awakening an agitated patient; and 3) the immediate high blood levels are associated with inducing more frequent and severe opioid withdrawal effects. Further, IV administration requires delivery by a trained professional, limiting the use of the drug to a small percentage of the population who can receive EMS care. Naloxone can be given by IM or SC injection, and has a more gradual onset of action because the drug must be absorbed from the muscle or skin. Although naloxone can also be given by IM or SC administration, the utility of delivering naloxone by lay persons using a needle is not common medical practice. There are currently no over-the-counter medications used by lay persons that require needle-based delivery. Thus, an unmet medical need is a needle-free delivery system capable of delivering naloxone in a properly designed product sufficient to achieve therapeutically effective blood levels of naloxone, and that can be used by a lay person accurately under intense emotional and environmental pressure to treat a person suspected of suffering an opioid overdose—most commonly an immediate family member or close acquaintance.

An additional problem with the current standard of care using naloxone to treat drug overdose is that the delivery of naloxone to patients in a state of drug overdose can result in a variety of responses in the drug overdosed patient. Depending on the route administered, naloxone can rapidly reverse the effects of the opioid, and in many instances, can induce instant and severe pain, nausea, vomiting, the occasional seizure, agitation, and/or combativeness. This can be dangerous both to the patient and to the emergency responder. Once awakened, the patient may be in a state of distress and uncertainty. Medical staff and/or the patient handling an unsheathed needle may risk puncture as a result of a disoriented or agitated patient. Thus, administration of a naloxone formulation, which would lessen a sudden reversal as observed using IV administration, is desired.

Finally, the current standard of care for a patient with a suspected opioid intoxication is to support ventilation and administer naloxone either IV, IM, or subcutaneously (SC). A demonstration of unmet medical need is the off-label administration of naloxone injection intranasally. The injection formulation, which is not formulated for intranasal use, has to be given intranasally via a separate mucosal atomizer device using ad hoc methods (Barton 2005, Kelly 2005, Kerr 2008, Merlin 2010, Robertson 2009, Sporer 2007). For example, the San Francisco EMS uses this drug administration technique as a standard-of-care to prevent needle-stick injuries to EMTs. While naloxone injection formulations currently administered intranasally by EMS personnel in the field as an opioid antidote using the FDA-approved parenteral product and a Mucosal Atomization Device ("MAD" device, available from Teleflex and/or LMA), there are numerous drawbacks that detract from the efficacy of the method. These include formulations not suited for intranasal delivery, a lack of a complete device containing naloxone and designed for intranasal delivery, and a lack of compositions specifically designed for manufacture with intranasal devices that do not utilize terminal autoclave sterilization, which can also be stored and conveniently and safely used and transported, a multi-step process to assemble the required elements subject to confusion and error, and which can be stored for long periods of time without causing product damage (i.e., fracturing of a glass container) or naloxone degradation resulting in the formation of 7,8-didehydronaloxone, a substance considered by the FDA to be undesirable/potentially genotoxic.

Further, currently formulations are not designed for nasal delivery However, Dowling, et al, "Population Pharmacokinetics of Intravenous, Intramuscular, and Intranasal Naloxone in Human Volunteers," Therapeutic Drug Monitoring, 30(4): 490-496 (2008) (hereafter "Dowling") describes the absorption and pharmacokinetics of a dilute naloxone injection type solution administered intranasally. The bioavailability was only 4%, suggesting that intranasal naloxone absorption is poor and leading a person skilled in the art away from the present invention. In fact, the authors in Dowling concluded that nasal delivery of naloxone was not feasible based on their results.

Due to the increasing need for opioid overdose reversal agents and methods, there is a need in the art for improved compositions and methods of delivery of such compositions. In particular, there is a need for integrating compositions, methods and devices that can allow for an effective reversal of opioid overdose, but which eliminates or minimizes the use of needles. There is further a need for effective formulations and methods of providing such compositions to an individual, for rapid absorption into the nasal mucosa and for reversing opioid overdose, that can be quickly and easily used, but which minimize sudden and severe side effects of rapid reversal of opioid overdose. Formulations having a concentration suited for delivery to and absorption by the naris (i.e., nostril or nasal passage) are also desired. Ideally, product designs are robust for use in many different environments, from austere to clinical environments, be ready to use, easy to understand and administer quickly, and durable and not subject to damage and breakage. Ideally, the formulations have minimal to no formation of 7,8-didehydronaloxone over accelerated or long term stability studies.

Further, there is a need for one-step, needle-free, portable naloxone delivery drug products that contain a sufficiently high concentration of naloxone but are capable of long term storage in a variety of different conditions, such that the naloxone is intact and effective when needed, and safe to deliver to a patient either by a professional or by an untrained layperson. It may be noted that the current use of nasal administration devices are intended for outpatient treatment in non-life threatening situations. In contrast, administration of naloxone for treatment of overdose is generally in the context of a high stress environment, and bystander administration of naloxone by non-medical persons is of questionable effectiveness, as nonmedical bystanders have limited ability and knowledge necessary to administer naloxone effectively. Clark, et al, "A Systematic Review of Community Opioid Overdose Prevention and Naloxone Distribution Programs" J. Addict Med 2014; 8: 153-163. Thus, a need in the art is for devices and formulations that can be easily administered by non-medical personnel.

The instant disclosure seeks to address one or more of these unmet needs in the art.

BRIEF SUMMARY

Disclosed herein are compositions comprising naloxone for intranasal delivery, methods of making such compositions, and devices for nasal delivery of naloxone compositions.

DETAILED DESCRIPTION

Definitions

Figure 1:
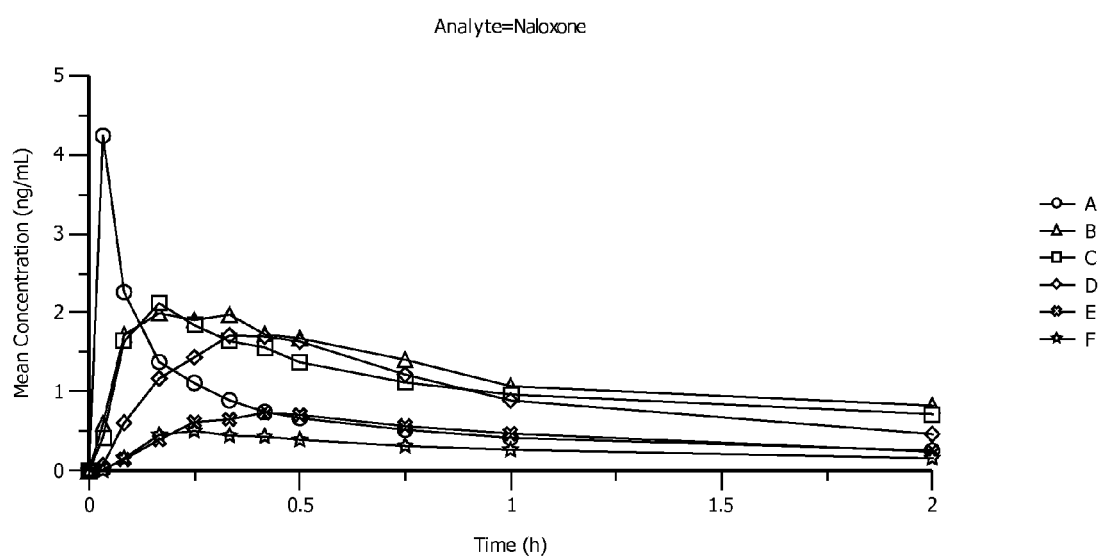
FIG. 1 is a graph depicting concentration-time data for the zero to two hour period plotted on a linear scale. Arm A=0.4 mg naloxone IV (intravenously); Arm B=1 mg naloxone IM (intramuscular injection); Arm C=1 mg naloxone SC (subcutaneous injection); Arm D=2 mg NNS (Naloxone Nasal Spray); Arm E=1 mg NNS (Naloxone Nasal Spray); Arm F=2 mg naloxone IN/MAD (Intranasal, Mucosal Atomization Device) (prior art).

The terms and expressions used herein have the ordinary meaning as is accorded to such terms and expressions with respect to their corresponding respective areas of inquiry and study except where specific meanings have otherwise been set forth herein.

The term "effective amount" means the amount of the formulation that will be effective in the treatment of a particular subject will depend on the particular subject and state of the subject, and can be determined by standard clinical techniques. In addition, in vitro or in vivo assays may optionally be employed to help identify optimal dosage ranges. The precise dose to be employed will also depend on the state of the patient, and should be decided according to the judgment of the practitioner and each patient's circumstances.

"IM" refers to intramuscular injection.

"IV" refers to intravenous injection.

"SC" refers to subcutaneous injection.

"IN/MAD" refers to the intranasal administration of a naloxone HCL injection composition (commercially available from IMS/Amphastar; also known as NARCAN®) using a mucosal atomization device (e.g., commercially available from TELEFLEX®). IN/MAD refers to the off-label use of the naloxone HCl injection in a mucosal atomization device as described, for example, in the document "Naloxone Training for Providers," by the City and County of San Francisco, Department of Public Health (Aug. 11, 2012).

"NNS" refers to the intranasal administration of the nasal naloxone spray shown in Table 1.

"Naloxone Related Substances" shall refer to a compound selected from the following: 10-α-hydroxynaloxone, oxymorphone, noroxymorphone, 10-β-hydroxynaloxone, 7,8-didehydronaloxone, 2,2'-bisnaloxone, and 3-O-allynlnaloxone.

The term "pharmaceutically acceptable" means approved by a regulatory agency of the Federal or a state government or listed in the U.S. Pharmacopeia or other generally recognized pharmacopeia or otherwise proven as safe for use in animals, mammals, and more particularly in humans.

As used herein, the term "stable" refers to physical, chemical, and microbiologic stability and which does not substantially decompose to form degradation products, e.g. adducts, when stored in a sealed package at about 25° C. at about 60% relative humidity for at least 12 months and up to 36 months or, at about 40° C. at about 75% relative humidity for at least 6 months and up to 36 months.

"Substantially free of" refers to formulations that are substantially free of certain ingredients or features described herein, provided that the remaining formula still contains all of the required ingredients or features as described herein. In this context, the term "substantially free" means that the selected composition contains less than a functional amount of the optional ingredient, typically less than 0.1% by weight, and also including zero percent by weight, of such optional or selected ingredient.

The formulas and corresponding methods may comprise, consist of, or consist essentially of the essential elements, steps, and limitations of the invention described herein, as well as any additional or optional ingredients, components, steps, or limitations described herein or otherwise useful in the compositions.

Disclosed herein are naloxone formulations that meet one or more of the aforementioned needs in the art. In particular, in certain aspects, Applicant has discovered formulations that may be particularly suited for nasal administration, may be of a concentration and in a composition suited for effective absorption by the nasal mucosa, and which may remain stable under stress conditions. Such formulations may be used in devices designed for nasal delivery without the need for needles or administration by a trained medical professional. Further, the disclosed compositions may be chemically stable and does not form 7,8-didehydronaloxone, a degradant considered potentially genotoxic by the FDA. In other aspects, the compositions are not harmful to the nasal mucosa.

In one aspect, Applicant has found that certain compositions comprising polymers, which typically would be used for nasal formulations for the purpose of increasing residence time of active on the mucosal membranes to allow a sustained period of delivery, result in a formulation that has poor stability. In particular, Applicant has found that formulations containing hypromellose, a commonly used polymer used in nasal formulations for its adhesive properties, for example, were less stable under stressed storage conditions than formulations without hypromellose.

In certain aspects, Applicant has further surprisingly found that the compositions described herein may effectively treat a subject via nasal administration at a pH from about 3.5 to about 5, or a pH of about 4. Specifically, naloxone is known to have a pKa of about 8. For nasal formulations, wherein transmucosal delivery is desired, it is generally considered advantageous, if not necessary, to ensure that an active agent is primarily in an un-ionized state, as unionized species pass through membranes more easily than ionized species. Naloxone, while most stable at lower pH levels such as between 3 and 5 would ideally be formulated at a pH near 8, so that the species are un-ionized and suited for crossing the nasal mucosa. The nasal mucosal is at a pH of about 5.5 to 6.5, a pH at which Applicant has found naloxone is unstable. Applicant has found, however, that the disclosed compositions can be formulated at a pH from about 3.5 to about 5.0, or at about 4, and that at this pH, the naloxone administered intranasally is surprisingly efficacious as compared to what would be expected based on the knowledge of the pKa and the need for the active agent to cross the mucosa. Applicant has also discovered the disclosed formulations do not damage the nasal mucosa at a pH of from about 3.5 to about 5.0.

In yet another aspect, Applicant has surprisingly found that the intranasal compositions and delivery systems disclosed herein can be used instead of naloxone injection for treating opioid overdose. As such, the compositions and delivery systems as disclosed herein are effective at reversing the hypoventilation and/or central nervous system depression occurring with opioid overdose while potentially decreasing the common side effects of severe agitation, nausea, vomiting, and the occasional seizure associated with IV administration. The peak serum levels of the disclosed compositions and methods are a surprising outcome in view of the art (in particular, Dowling), and address an important need in the art.

Naloxone

The disclosed compositions may comprise an opioid antagonist, such as naloxone, naltrexone, nalmefene, nalorphine, nalbuphine, naloxoneazinen, methylnaltrexone, ketylcyclazocine, norbinaltorphimine, naltrindol, 6-β-naloxol, 6-β-naltrexol, or pharmaceutically acceptable salts thereof. In one embodiment, the opioid antagonist is naloxone, naloxone base, or a pharmaceutically acceptable salt thereof, including naloxone HCl, naloxone HCl dihydrate, or combinations thereof. Naloxone hydrochloride is a synthetic congener of oxymorphone. In structure it differs from oxymorphone in that the methyl group on the nitrogen atom is replaced by an allyl group. It is known chemically as 17-allyl-4,5α-epoxy, 3-14-dihydroxymorphinan-6-one hydrochloride. It has a molecular weight of 363.84, and the following structural formula:

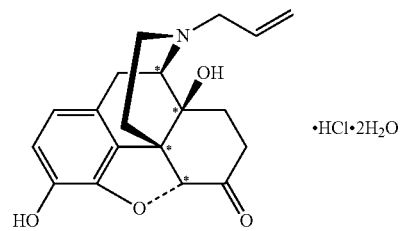

Naloxone contains four chiral centres (*).

Naloxone hydrochloride occurs as a white to slightly off-white powder, and is soluble in water, in dilute acids, and in strong alkali; slightly soluble in alcohol; practically insoluble in ether and in chloroform. Naloxone prevents or reverses the effects of opioids including respiratory depression, sedation and hypotension. Also, it can reverse the psychotomimetic and dysphoric effects of agonist-antagonists such as pentazocine. Naloxone is an essentially pure opioid antagonist, i.e., it does not possess the "agonistic" or morphine-like properties characteristic of other opioid antagonists. When administered in usual doses in the absence of opioids or agonistic effects of other opioid antagonists, it exhibits essentially no pharmacologic activity. Naloxone has not been shown to produce tolerance or cause physical or psychological dependence. In the presence of physical dependence on opioids, naloxone will produce withdrawal symptoms. However, in the presence of opioid dependence, withdrawal symptoms will appear within minutes of naloxone administration and will subside in about 2 hours. The severity and duration of the withdrawal syndrome are related to the dose and route of administration of naloxone and to the degree and type of dependence. While the mechanism of action of naloxone is not fully understood, in vitro evidence suggests that naloxone antagonizes opioid effects by competing for the mu, kappa, and sigma opiate receptor sites in the CNS, with the greatest affinity for the mu receptor.

Naloxone Compositions

In one aspect, the disclosed compositions may comprise from about 5 mg/mL to about 50 mg/mL, or from about 10 mg/mL to about 40 mg/mL, or from about 15 mg/mL to about 30 mg/mL, or from about 10 mg/mL to about 20 mg/mL of an opioid antagonist. In another aspect, the disclosed compositions may comprise from about 5 mg/mL to about 15 mg/mL, or from about 8 mg/mL to about 12 mg/mL, or about 9 mg/mL to about 11 mg/mL, or about 9 mg/mL to about 10 mg/mL, or about 9 mg/mL, or about 10 mg/mL of an opioid antagonist. The opioid antagonist may be naloxone or a pharmaceutically acceptable salt thereof. In one aspect, the opioid antagonist may be naloxone, naloxone HCl, or naloxone HCL dihydrate. Unless otherwise specified, the term "naloxone," as used herein, refers to naloxone, naloxone HCl, naloxone HCl dihydrate, any pharmaceutically acceptable salt of naloxone, or combinations thereof. In other aspects, other opioid antagonists, such as naltrexone, nalmefene, nalorphine, nalbuphine, naloxoneazinen, methylnaltrexone, ketylcyclazocine, norbinaltorphimine, naltrindol, 6-β-naloxol, 6-β-naltrexol or pharmaceutically acceptable salts thereof, may be used.

In one aspect, the composition may comprise naloxone at a concentration of from about 0.7 to about 0.9, or about 0.85 to about 0.9, or about 0.81 mg/100 µL; In one aspect, the composition may comprise naloxone HCl dihydrate at a concentration of from about 0.9 to about 1.1, or about 0.95 to about 1.1, or about 1.0 mg/100 µL; In one aspect, the composition may comprise naloxone HCl at a concentration of from about 0.8 to about 1.0; or about 0.91 mg/100 µL.

The composition may further comprise from about 5 mM to about 50 mM, or from about 10 to about 40 mM, or from about 25 mM to about 30 mM, or about 25 mM of a buffer. The buffer may comprise citric acid. Other suitable buffers may be readily understood by one of ordinary skill in the art.

In one aspect, the composition may comprise from about 2 mM to about 20 mM, or from about 5 mM to about 15 mM, or from about 8 mM to about 12 mM, or about 10 mM disodium ethylene diamine tetraacetic acid (EDTA).

In certain aspect, the composition may further comprise from about 0.1 weight % to about 2 weight %, or about 0.2 weight % to about 1.0 weight %, or about 0.5 weight % of an antimicrobial agent. The antimicrobial agent may comprise an alcohol antimicrobial agent. In one aspect, the antimicrobial agent may comprise benzyl alcohol. Other suitable antimicrobial agents may be readily understood by one of ordinary skill in the art.

In one aspect, the disclosed compositions are formulated such that administration of the compositions, when administered intranasally, results in a $T_{max}$ in a subject from about 0.1 hours to about 0.5 hours, or from about 0.3 hours to about 0.5 hours, or about 0.2 hours, or about 0.3 hours, or about 0.4 hours, or about 0.5 hours after intranasal administration. In one aspect, the compositions may result in a peak concentration ($C_{max}$) of from about 1.0 ng/mL to about 4.0 ng/mL, or from about 1.2 ng/mL to about 3 ng/mL, or from about 1.5 ng/mL to about 2 ng/mL at a time period of about 15 minutes to about 20 minutes after intranasal administration.

In one aspect, intranasal administration of 100 µL of the disclosed compositions results in an $AUC_{0-inf}$ of from about 1 to about 2 ng-hr/mL. In other aspects, intranasal administration of 200 µL of the disclosed composition results in an $AUC_{0-inf}$ of from about 2.5 to about 4.5, or from about 3 to about 4, or about 3.5 ng-hr/mL.

The composition of claim 1, wherein administration of said composition intranasally results in a parameter selected from a $T_{max}$ of about 0.1 hours to about 0.5 hours in a subject; a peak plasma concentration of from about 1.0 to about 4.0 ng/mL at a time period of from about 5 to about 30 minutes after administration; and combinations thereof.

In one aspect, the administration of about 200 µL of the disclosed composition administers about 2 mg of an opioid antagonist, in particular naloxone, naloxone HCl, and/or Naloxone HCl dihydrate, intranasally, and results in an $AUC_{0-inf}$ of from about 2.5 to about 4.5 ng-hr/mL, or about 2.5 to about 2.7 ng-hr/mL, or about 2.6 ng-hr/mL.

In one aspect, the administration of about 200 µL of the disclosed composition administers about 2 mg of an opioid antagonist, in particular naloxone, naloxone HCl, and/or Naloxone HCl dihydrate, intranasally, and results in a Cmax of from about 1 to about 3 or about 1.5 to about 2.5 or about 1.8 ng/mL.

In one aspect, the composition may comprise sodium chloride in an amount sufficient to adjust the osmolality of the compositions to from about 300 to about 500, or from about 350 to about 450, or about 400.

The compositions may further comprise sodium hydroxide or hydrochloric acid in an amount sufficient to adjust the pH to from about 3 to about 5.5, or from about 3.5 to about 5, or about 4±0.5.

In one aspect, the compositions may be substantially free of a paraben preservative. Paraben preservatives may include methylparaben, ethylparaben, propylparaben, butylparaben, heptylparaben, isobutyparaben, isopropylparaben, benzylparaben, sodium salts thereof, and combinations thereof. In one aspect, the compositions are substantially free of methyl paraben, propyl paraben, and combinations thereof. Other paraben preservatives will be readily understood by one of ordinary skill in the art.

In one aspect, the compositions may be substantially free of a viscoelastic polymer, wherein the viscoelastic polymer may be selected from a cellulose-based material. In one aspect, the composition may be substantially free of hydroxypropyl methylcellulose (hypromellose). Other viscoelastic polymers and/or cellulose-based material will be readily understood by one of ordinary skill in the art.

In one aspect, the composition may be substantially free of other commonly added excipients. Such excipients may include, for example, glycerine, propylene glycol, sorbitol, ascorbic acid, or the like.

The compositions are formulated with a suitable carrier to form a pharmaceutically acceptable nasal spray. In one aspect, the carrier may comprise water, saline, dextrose, or other suitable aqueous or non-aqueous carriers suitable for application to the nasal mucosa. In one aspect, the nasal spray is formed with an aqueous carrier, such as water or saline. Other suitable carriers will be readily understood by one of ordinary skill in the art.

In one aspect, the composition may comprise less than about 0.1% of any individual Naloxone Related Substance, or less than 0.05% of any individual Naloxone Related Substance, or, in another aspect, the compositions may be substantially free of any individual Naloxone Related Substance, as measured after storage at 40° C./75% RH for at 6 months and assayed by European Pharmacopoeia Naloxone Hydrochloride Dihydrate monograph RP-HPLC method. In one aspect, the composition is substantially free of the Naloxone Related Substance 7,8-didehydronaloxone.

In one aspect, the compositions may be stable at room temperature (25° C./60% RH) for at least about 6 months, or at least about 9 months, or at least about 12 months. In another aspect, the compositions may be stable at 40° C./75% RH for at least about 6 months, or at least about 9 months, or at least about 12 months, and in a yet further aspect, at least 24-36 months at room temperature (25° C./60% RH).

In one aspect, the water/solvent of the composition may be sparged with nitrogen to remove dissolved oxygen. The composition may be covered with a nitrogen head space prior to placing the composition into the nasal spray container.

In one aspect, an aseptic composition is disclosed. In this aspect, the composition may comprise from 5 mg/mL to 50 mg/mL of an opioid antagonist selected from naloxone, naloxone HCl, naloxone HCl dihydrate, or a combination thereof; from 5 mM to 50 mM of a buffer; from 2 to 20 mM disodium ethylene diamine tetraacetic acid (EDTA); and a carrier. In other aspects the aseptic composition may comprise naloxone at a concentration of from about 0.7 to about 0.9, or about 0.85 to about 0.9, or about 0.81 mg/100 μL; from 5 mM to 50 mM of a buffer, for example citric acid; from 2 to 20 mM disodium ethylene diamine tetraacetic acid (EDTA); and a carrier. In one aspect, the aseptic composition may comprise naloxone HCl dihydrate at a concentration of from about 0.9 to about 1.1, or about 0.95 to about 1.1, or about 1.0 mg/100 μL; from 5 mM to 50 mM of a buffer, for example citric acid; from 2 to 20 mM disodium ethylene diamine tetraacetic acid (EDTA); and a carrier. In one aspect, the aseptic composition may comprise naloxone HCl at a concentration of from about 0.8 to about 1.0; or about 0.91 mg/100 μL; from 5 mM to 50 mM of a buffer, for example citric acid; from 2 to 20 mM disodium ethylene diamine tetraacetic acid (EDTA); and a carrier. In such aseptic formulations, an antimicrobial is not necessary, such that the formulations may be substantially free of an antimicrobial, or substantially free of benzyl alcohol.

Methods of Use

In one aspect, methods of using the disclosed compositions naloxone are disclosed. The methods and devices disclosed herein are suited for use by both medical and non-medical personnel.

In one aspect, disclosed are methods of treating a known or suspected opioid overdose in a subject in need thereof, comprising administering a composition as disclosed herein, wherein the composition is administered intranasally via the nasal membranes to the subject. In one aspect, disclosed are methods for the complete or partial reversal of opioid intoxication, comprising administering a composition as disclosed herein, wherein the composition is administered intranasally via the nasal membranes to the subject. In one aspect, the subject may be administered a dose, per naris, of from about 0.1 to about 2.0, or from about 0.2 to about 1.5, or about 0.81 mg of naloxone, or from about 0.1 to about 2.0, or from about 0.2 to about 1.5, or about 1.0 mg of naloxone HCl dihydrate; or from about 0.1 to about 2.0, or from about 0.2 to about 1.5, or about 0.91 mg of naloxone HCl.

One of ordinary skill in the art will readily recognize that one or more administration steps may be carried out. In one aspect, the known or suspected opioid overdose is manifested by respiratory and/or central nervous system depression. The phrase "treating an opioid overdose" includes "reversing the effects of an opioid overdose".

In another aspect, the compositions described herein can be used to diagnosis suspected or known acute opioid overdose. In yet another aspect, the compositions described herein can be used to increase blood pressure in the management of septic shock, generally as an adjunctive agent to other drugs.

In one aspect, the administration results in a $T_{max}$ in a subject from about 0.1 hours to about 0.5 hours, or from about 0.3 hours to about 0.5 hours, or about 0.2 hours, or about 0.3 hours, or about 0.4 hours, or about 0.5 hours after intranasal administration.

The method may utilize any nasal spray device known in the art, such as a needle-free device or a "ready-to-use" device, wherein minimal or no manipulations are required to use the device and administer the composition into a nostril. The nasal spray device, in some aspects, may be a disposable device suitable for placement in household trash and not requiring formal hazardous waste disposal as is true for needle-based delivery. In one aspect, the device used allows for administration of a volume of from about 50 μL to about 250 μL, or from about 75 μL to about 200 μL, or from about 80 μL to about 120 μL, or from about 90 μL to about 110 μL, or from about 100 μL to about 150 μL, or about 100 μL, or about 180 μL to about 220 μL, or about 200 μL.

In one aspect, a method of treating a known or suspected opioid overdose is disclosed. The method may comprise the step of intranasally administering a composition as described herein to an individual in need thereof, wherein the composition is administered via the nasal membranes to the individual; wherein the individual is administered a dose, per naris, of from about 0.1 to about 2 mg.

In one aspect, the known or suspected opioid overdose may be manifested by respiratory and/or central nervous system depression.

In one aspect, the intransal administration results in a $T_{max}$ of about 5 to about 30 minutes. The method may utilize a device having a property selected from needle-free, ready-to-use, disposable, or a combination thereof. In some aspects, the administration step may comprise intranasal administration of a single spray per naris, wherein said spray may be repeated as necessary. In some aspects, the composition may be administered in a volume of from about 50 μL to about 250 μL.

In one aspect, a method for reversing the effects of an opioid overdose in an individual in need thereof is disclosed, which may comprise the step of administering intranasally a dose of a naloxone composition, wherein the naloxone composition may comprise about 10 mg/mL naloxone HCl dihydrate, about 25 mM citric acid, about 10 mM EDTA, and about 0.5% benzyl alcohol; wherein said dose comprises about 200 μL of said naloxone composition; and wherein said dose is divided into two half doses; wherein each said half dose comprises about 100 μL of said composition; and wherein each said half dose may be administered intranasally to a subject in need thereof.

Methods of Manufacture

The compositions described herein may be manufactured according to methods as are commonly understood in the art.

Device

The disclosed nasal spray device, as set forth above, is intended for use by both medical and non-medical personnel. In particular, the device may have one or more features selected from being single-use, needle-free, ready-to-use, disposable, and combinations thereof. The device may be configured to administer the disclosed compositions as a single spray per naris. The device may comprise one or more unit dose containers, each container delivering about one 100 μL spray containing about 1 mg naloxone HCl dihydrate (a 10 mg/mL solution) or a 2 mg naloxone hydrochloride dihydrate in 100 μL. In other aspects, the devices may be modified to deliver amounts of between about 50 μL to about 200 μL spray, and may utilize solutions of varying concentration, for example from about 5 mg/mL to about 20 mg/mL, or about 7 mg/mL to about 15 mg/mL. Any nasal spray device known in the art can be used to deliver the nasal spray and compositions described herein. In one aspect, the nasal spray device is an Aptar/Pfeiffer Unitdose device (available from Aptar Pharma, Congers, N.Y., http://www.aptar.com/pharma/prescription-division/products/uds). The naloxone nasal spray may comprise a preserved solution with pH and osmolality appropriate for nasal administration. Similarly, it could be prepared as a sterile solution without an antimicrobial preservative.

In one aspect, the Aptar/Pfeiffer Unitdose delivery device may be used to deliver the disclosed compositions. In one aspect, the nasal spray device delivers a volume of about 100 μL per spray. This delivery system is used in other approved nasal spray drug products in the U.S. (Imitrex nasal spray NDA #20-626). The direct product contact components of the container closure may comprise a container (glass vial), manufactured using FIOLAX glass by MGLAS or NUOVA OMPI, a plunger (Stopper), manufactured by West Pharmaceuticals using PH 701/55/C Black Chlorobutyl Rubber, and a cannula (included in Unitdose delivery device), manufactured by Acti-Med using 1.4301/AISI 304 Stainless steel.

Naloxone HCl dihydrate nasal spray, 10 mg/mL, 100 µL/spray, assembled into the Aptar/Pfeiffer Unitdose delivery device or in vials (not assembled into the delivery device) may be stored protected from light. Bulk vials and assembled Unitdose delivery device units of drug product may be stored in bulk sealed containers pending further processing. The disclosed compositions may be assembled in the Unitdose delivery devices and packaged in 4"×4" foil pouches, one device/pouch, heat-sealed and labeled as appropriate. Other secondary packaging commonly used in industry may also suffice, and will be readily appreciated by one of ordinary skill in the art.

In one aspect, the device for nasal administration of an opioid antagonist may provide a unit dose, wherein the unit dose comprises about 80 µL to about 120 µL of a disclosed composition, or about 90 µL to about 110 µL of a disclosed composition, or about 100 µL of a disclosed composition. In another aspect, the unit dose comprises about 200 µL of a disclosed composition, where the unit dose may be divided into two half doses. Each half dose may comprise about 100 µL of a disclosed composition, such that administration of the two half doses results in a total administration of about 200 µL of the composition. The unit dose may comprise naloxone at a concentration of from about 0.7 to about 0.9, or about 0.85 to about 0.9, or about 0.81 mg/100 µL; or naloxone HCl dihydrate at a concentration of from about 0.9 to about 1.1, or about 0.95 to about 1.1, or about 1.0 mg/100 µL; or naloxone HCl at a concentration of from about 0.8 to about 1.0; or about 0.91 mg/100 µL.

In one aspect, disclosed is a device for administration of naloxone, containing a composition as disclosed herein, wherein the device has a feature selected from single-use, needle-free, ready-to-use, disposable, and combinations thereof.

In one aspect, disclosed is a device for nasal administration of naloxone to an individual in need thereof, wherein the device contains a composition comprising about 10 mg/mL naloxone HCl dihydrate, about 25 mM citric acid, about 10 mM EDTA, and about 0.5% benzyl alcohol; wherein said composition is provided in a dose for nasal administration to a subject in need thereof; wherein said dose comprises about 200 µL of the composition; wherein said dose is divided into two half doses; wherein each said half dose comprises about 100 µL of said composition; and wherein each said half dose may be administered intranasally to a subject in need thereof.

In one aspect, a nasal spray is disclosed. The nasal spray may comprise (i) about 7 mg/mL to about 11 mg/mL naloxone or a pharmaceutically acceptable salt thereof; (ii) about 20 mM to about 30 mM citric acid; (iii) about 5 mM to about 15 mM ethylenediaminetetraacetic acid; and (iv) about 0.2% to about 1.0% benzyl alcohol; wherein the nasal spray has a pH from about 3 to about 5.5. The nasal spray may comprise naloxone or pharmaceutically acceptable salt thereof, or may comprise naloxone hydrochloride dihydrate. In one aspect, the nasal spray may comprise (i) about 10 mg/mL naloxone hydrochloride dihydrate; (ii) about 25 mM citric acid; (iii) about 10 mM ethylenediaminetetraacetic acid; and (iv) about 0.5% benzyl alcohol; wherein the nasal spray has a pH from about 3.5 to 5.0.

In one aspect, a nasal unit dosage that may comprise from about 80 µL to about 120 µL, or about 90 µL to about 110 µL of the nasal spray is disclosed.

In one aspect, a nasal spray device comprising from about 80 µL to about 120 µL, or about from about 90 µL to about 110 µL of the nasal spray is disclosed.

Kit

In other aspects, a kit comprising a nasal spray device as described herein is disclosed. In one aspect, the kit may comprise one or more devices as disclosed herein, containing a disclosed composition, wherein the device is sealed within a container sufficient to protect the device from atmospheric influences. The container may be, for example, a foil, or plastic pouch, particularly a foil pouch, or heat sealed foil pouch. Suitable containers sufficient to adequately protect the device will be readily appreciated by one of skill in the art.

In one aspect, the kit may comprise one or more devices as disclosed herein, wherein the device may be sealed within a first protective packaging, or a second protective packaging, or a third protective packaging, that protects the physical integrity of the nasal spray product. One or more of the first, second, or third protective packaging may comprise a foil pouch. The kit may further comprise instructions for use of the device. In one aspect, the kit contains two nasal spray devices.

In one aspect, the kit may comprise a device as disclosed herein, and may further comprise instructions for use. In one aspect, the instructions may comprise visual aid/pictorial and/or written directions to an administrator of the device. The directions may include the steps of a) placing the individual on their back;
b) inserting a first sprayer into the individual's nostril;
c) aiming the nozzle towards the side of the individual's nose and away from the center of the nose;
d) pressing a plunger of the device firmly with the thumb of the administrator;
e) repeating steps b through d with a second sprayer in the second nostril of the individual's nose;
f) monitoring the individual and the breaths of the individual, wherein if the individual does not improve or if signs of opioid overdose reappear 3-5 minutes after administering the composition, the administrator repeats the steps of b through e with a second device. The term "does not improve" means wherein the individual does not exhibit increased breathing rates, for example, wherein an individual does not achieve 10 to 12 breaths per minute within about 3 to about 5 minutes after administration.

The instructions may further comprise instructions, in words or in pictures, to the administrator having the steps of supporting the person's head so that they can breathe easily; removing the sprayers from the package; holding the sprayer gently with fingers and thumb, using both sprayers in a package; using each sprayer only once; using one sprayer for each nostril; contacting 911, getting medical assistance urgently, or transporting the individual for medical care; observing the individual for improvement, wherein if the individual does not improve, a second set of sprayers is used to administer the composition to the individual.

The kit may comprise two nasal spray devices and instructions for use; wherein each nasal spray device comprises from about 80 µL to about 120 µL of a disclosed nasal spray, or from about 90 µL to about 110 µL of a disclosed nasal spray.

EXAMPLES

Example 1

Exemplary Compositions and Materials

TABLE 1

Composition of a Single Spray of Naloxone HCl Dihydrate Nasal Spray, 10 mg/mL ("NNS")

| Component | CAS # | Amount per Unitdose Actuator Dose - 100 uL | Function | Quality Standard |
|---|---|---|---|---|
| Naloxone HCl dihydrate | N/A | 1.0 mg | Active | USP, EP, BP |
| Citric Acid, anhydrous | 77-92-9 | 0.48 mg | Buffer | USP, Ph. Eur. |
| Disodium EDTA dihydrate | 6381-92-6 | 0.372 mg | Preservative | USP, Ph. Eur. |
| Benzyl Alcohol | 100-51-6 | 0.5 mg | Preservative | NF, Ph. Eur. |
| Sodium Chloride | 7647-14-5 | q.s.* | Adjust Osmolality | USP |
| Purified Water, USP | 7732-18-5 | q.s. to 100 uL | Inactive/ Carrier | USP |
| Hydrochloric Acid | 7647-01-0 | q.s. pH to 4.25 ± 0.10 | pH Adjustment | USP, Ph. Eur. |
| Sodium Hydroxide | 1310-73-2 | q.s. pH to 4.25 ± 0.10 | pH Adjustment | USP, Ph. Eur. |
| Nitrogen Gas** | | | Compounding Overlay | USP, NF |

*Osmolality is adjusted to 385-425 mOsm prior to final q.s. with Purified Water to yield final osmolality within 365-425, an in process specification requirement prior to vial filling.
**Nitrogen gas used to purge purified water prior to compounding, as overlay during compounding and as an overlay in the hold tank.

TABLE 2

Exemplary Naloxone Compositions

| Component | Example No. | | | | | | | | | |
|---|---|---|---|---|---|---|---|---|---|---|
| | 1* | 2 | 3 | 4 | 5 | 6** | 7 | 8 | 9 | 10 |
| Naloxone (mg/mL) | 10 | 10 | 10 | 10 | 10 | 20 | 20 | 20 | 20 | 20 |
| Citric Acid (%) | 0.5 | 0.1 | 0.25 | 0.75 | 1.0 | 0.5 | 0.1 | 0.25 | 0.75 | 1.0 |
| Disodium EDTA dehydrate (%) | 0.4 | 0.2 | 0.3 | 0.5 | 0.6 | 0.4 | 0.2 | 0.3 | 0.5 | 0.6 |
| Benzyl Alcohol (%) | 0.5 | 0.25 | 0.38 | 0.63 | 0.75 | 0.5 | 0.25 | 0.38 | 0.63 | 0.75 |
| Sodium Chloride | To an osmolality of 365-425 mOsm | | | | | | | | | |
| Purified Water | Balance of composition | | | | | | | | | |
| Hydrochloric Acid | As needed to adjust pH to 4.0 | | | | | | | | | |
| Sodium Hydroxide | As needed to adjust pH to 4.0 | | | | | | | | | |
| Nitrogen | Overlay | | | | | | | | | |

Example 2

Methods of Making Exemplary Compositions

TABLE 3

Exemplary Formulation Method. The following components are used to prepare Naloxone HCl Nasal Spray ("NNS") bulk formulation in a 10 kg scale.

| Component | Quality Standard | Quantity Required for 10 Kg Batch | Nominal Concentration in 10 Kg Batch | % of 10 Kg Batch |
|---|---|---|---|---|
| Naloxone HCl dihydrate | USP, Ph Eur, BP | 100 g | 10 mg/mL | 1.00% |
| Citric Acid, anhydrous | USP, Ph Eur | 48 g | 25 mM | 0.48% |
| Disodium EDTA dihydrate | USP, Ph Eur | 37.2 g | 10 mM | 0.37% |
| Benzyl Alcohol | NF, Ph Eur | 50 g | 0.50% | 0.50% |
| Sodium Chloride | USP | | q.s.* | |
| Purified Water | USP | | q.s. | |
| HCl 1N** | USP, Ph Eur | As needed | q.s.** | |
| NaOH 1N** | USP, Ph Eur | As needed | q.s.** | |
| Nitrogen | USP, NF | Overlay | | |

*Sodium Chloride added as needed to bring Osmolality to 365-425 mOsm
**Added as needed to adjust pH to 4.25 ± 0.10 during formulation Manufacturing is conducted in a controlled environment using equipment and facilities that are operated in compliance with cGMP. Naloxone HCl can be manufactured at commercial scale using the same process used for clinical at a 10 kg scale using the following process:

1. Prepare dedicated 20 lL stainless vessel, mixer, and blade
2. Compound excipients with mixing and nitrogen blanket
   a. Add nitrogen-purged USP purified water—8500 g
   b. Add citric acid—48 g
   c. Add disodium EDTA dihydrate—37.2 g
   d. Add benzyl alcohol—50 g
3. Adjust pH to 4.25 with 1 N NaOH (1N HCl available, if required)
4. Add naloxone HCl dihydrate—100 g a. Mix until dissolved
5. Verify pH to 4.25 and adjust if necessary, with 1 N NaOH or 1 N HCl solutions
6. Add nitrogen-purged USP purified water to bring batch weight to 9500 g.
7. Check osmolality and add NaCl to bring to within 365-425 mOsm
8. Add nitrogen-purged USP purified water to q.s. weight to 10,000 g
9. Transfer with peristaltic pump through 0.22 µm supor filter into a 20l hold tank.

During the compounding of the formulation, pH is adjusted to a target of 4.25±0.1 prior to the addition of naloxone HCl and verified. Prior to final Q.S. with 5% of target batch weight, the osmolality is measured and the compounded solution is adjusted with NaCl to a target osmolality between 385 and 425 mOsm. Additionally, in-process testing is performed to assess the bulk formulation post-filtration and prior to vial filling by the laboratory for analysis of pH, osmolality (365-425 mOsm), specific gravity.

10. Product may be held overnight at room temperature under a nitrogen blanket prior to filling.
11. Vials are filled to deliver 100 µL using the Aptar/Pfeiffer single spray device. The product is filtered through a 0.22 µm Supor filter after formulation and prior to being filled into vials.

Vial filling is performed using a SFM5110 Bausch and Stroebel semi-automated vial filling line. Filled vials are subsequently assembled into the Aptar/Pfeiffer unit dose delivery device using an Ima F57 assembly line.

Example 3

Pharmacokinetic Data

Pharmacokinetic parameters for naloxone administered by using conventional FDA-approved products, routes of delivery and doses were compared to a naloxone nasal spray drug product. In addition, naloxone pharmacokinetic parameters were studied after using an FDA-approved naloxone injection product given by a common, but not approved, route of delivery by a nasal atomizer device. The study arms and doses are outlined below.

Treatment A: 0.4 mg Naloxone HCl injection solution administered by intravenous (IV) injection [0.4 mg IV]
Treatment B: 1 mg Naloxone HCl injection administered by IM deltoid muscle injection [1 mg IM]
Treatment C: 1 mg Naloxone HCl injection administered by SC injection on the arm [1 mg SC]
Treatment D: 2 mg NNS using 2 sprays of 1 mg/100 uL naloxone HCl (1 spray [1 mg/100 uL] in each nostril) [2 mg NNS, 10 mg/mL]
Treatment E: 1 mg NNS solution using 1 spray of 1 mg/100 uL Naloxone HCl (1 spray [1 mg/100 uL] in the right nostril) [1 mg NNS]
Treatment F: 2 mg/2 mL Naloxone HCl injection composition (obtained from IMS/Amphastar) administered by intra-nasal delivery via Mucosal Atomization Device (1 mL/nostril) [2 mg IN/MAD]. Treatment F represents the current off-label medical practice of administering 2 mg naloxone injection intranasally using the 510(k)-cleared Mucosal Atomization Device.

This outpatient study enrolled a total of 20 volunteers. Thirteen volunteers were enrolled in a flexible 5-way crossover design. One subject did not complete the crossover, so 12 subjects received treatments A through E, above. Six different subjects received only one treatment, treatment F, consisting of 2 mg of marketed injectable naloxone by intranasal administration using the commercially available Mucosal Atomization Device (IN/MAD). One subject who was treated in arms A-E also received treatment F.

Blood samples for naloxone were collected from each subject according to the following schedule: 0 (predose), 2, 5, 10, 15, 20, 25, 30 and 45 minutes, and 1, 2, 4 and 8 hours after naloxone HCl administration. A validated LC/MS/MS bioassay was used for quantitation of free naloxone concentrations. The pharmacokinetic data for $T_{max}$, $C_{max}$, and AUC and other variables were generated (using WINNONLIN), consistent with FDA BA/BE guidances, to understand relative exposure and to design a pivotal comparative bioavailability trial.

Vital sign measurements included: blood pressure, respiratory rate, and heart rate. Vital signs were measured and recorded at baseline then every 15 minutes until one hour and then at the 2, 3, 4 and 8 hour post-dose time-points. Temperature was measured at baseline and at 2, 4 and 8 hours.

Pre- and post-dose nasal exams were performed by the same evaluator to minimize rater variability in assessment. Nasal examinations were performed at screening, prior to and approximately 4-6 hours after nasal (IN) Naloxone HCl administration, as well as post-treatment examinations to evaluate the nasal safety of the naloxone nasal spray (NNS).

Pilot Study Results

The pilot study showed that the $T_{max}$ was achieved most quickly after IV administration, as expected. The $T_{max}$ was achieved at 20 minutes (0.33 hr) after IM administration and 25 minutes (0.42 hr) after 2 mg Naloxone Nasal Spray administration. The serum levels in the 2 mg Naloxone Nasal Spray group demonstrated a later peak with a slower increase over the initial 15 minutes as compared to high levels seen after IV administration. The slower increase in blood serum levels is likely to be effective at reversing the hypoventilation while potentially decreasing the common side effects of severe agitation, nausea, vomiting, and the occasional seizure after IV administration. The relatively lower peak of naloxone serum levels with the use of IN/MAD was the most surprising. As expected, the $C_{max}$ was highest after IV administration and lowest after the 2 mg IN/MAD administration. Surprisingly, it was found that administration of the NNS formulations as a 2 mg dose had a maximum concentration that was four times that of the 2 mg IN/MAD administration and an area under the curve (a measure of total systemic exposure) 3.5 times the IN/MAD administration.

Pharmacokinetic Study Outcomes

Figure 2:
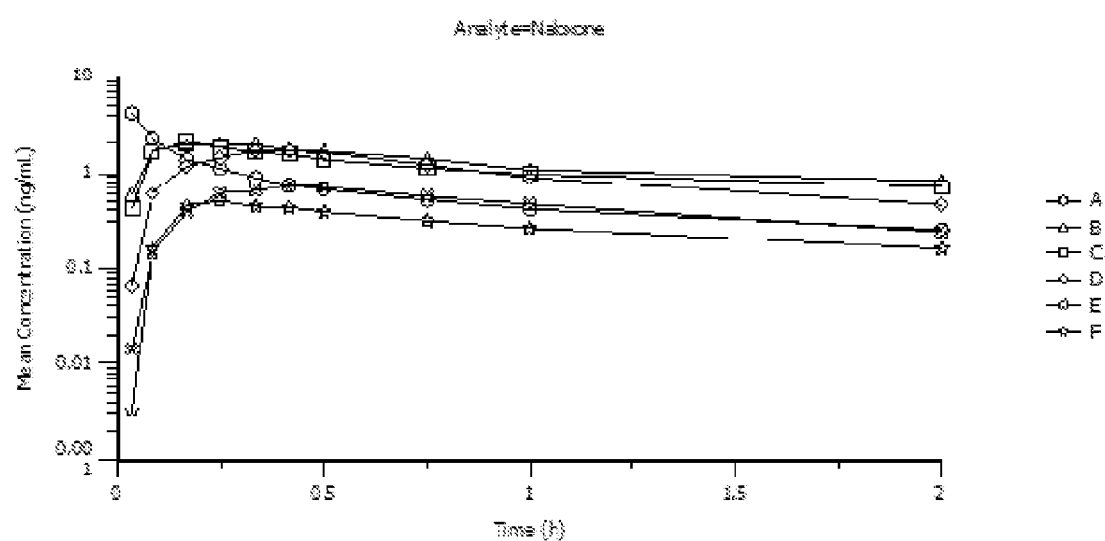
FIG. 2 is a graph depicting concentration-time data for the zero to two hour period plotted on a semi-logarithmic scale.

The principal outcomes of the study are described in Tables 4-11 and graphs in FIGS. 1-2.

TABLE 4

PK Parameters from Study
Median ± SD

| | Arm | $t_{max}$ (hr) | $C_{max}$ (ng/mL) | $AUC_{0-inf}$ (ng-hr/mL) | $t_{1/2}$ (hr) |
|---|---|---|---|---|---|
| A | 0.4 mg IV | 0.03 ± 0.06 | 3.87 ± 2.72 | 1.67 ± 0.54 | 1.28 ± 0.17 |
| B | 1 mg IM | 0.33 ± 0.52 | 2.54 ± 1.04 | 4.43 ± 1.16 | 1.41 ± 0.32 |
| C | 1 mg SC | 0.17 ± 0.29 | 2.72 ± 0.79 | 4.15 ± 1.07 | 1.59 ± 0.60 |

TABLE 4-continued

PK Parameters from Study
Median ± SD

| | Arm | $t_{max}$ (hr) | $C_{max}$ (ng/mL) | $AUC_{0-inf}$ (ng-hr/mL) | $t_{1/2}$ (hr) |
|---|---|---|---|---|---|
| D | 2 mg NNS | 0.42 ± 0.25 | 1.95 ± 1.05 | 3.47 ± 0.80 | 1.53 ± 0.17 |
| E | 1 mg NNS | 0.50 ± 0.20 | 0.84 ± 0.49 | 1.52 ± 0.45 | 1.41 ± 0.31 |
| F | 2 mg IN/MAD | 0.27 ± 0.11 | 0.53 ± 0.16 | 0.90 ± 0.17 | 1.64 ± 0.30 |

TABLE 5

ANOVA for Comparing Doses and Routes of Naloxone Injection to Naloxone Nasal Spray 2 mg.

| Analyte | Dependent | Reference | Test | Ratio % Ref | CI 90% lower | CI 90% upper |
|---|---|---|---|---|---|---|
| Naloxone | $Ln(C_{max})$ | D | A | 220 | 170 | 283 |
| Naloxone | $Ln(AUC_{last})$ | D | A | 57 | 49 | 67 |
| Naloxone | $Ln(AUC_{inf})$ | D | A | 59 | 51 | 68 |
| Naloxone | $Ln(C_{max})$ | D | B | 134 | 104 | 173 |
| Naloxone | $Ln(AUC_{last})$ | D | B | 154 | 132 | 179 |
| Naloxone | $Ln(AUC_{inf})$ | D | B | 154 | 133 | 179 |
| Naloxone | $Ln(C_{max})$ | D | C | 130 | 101 | 168 |
| Naloxone | $Ln(AUC_{last})$ | D | C | 141 | 121 | 164 |
| Naloxone | $Ln(AUC_{inf})$ | D | C | 145 | 125 | 168 |

TABLE 6

Descriptive Statistics for Naloxone Concentration-Time Data after Administration of 0.4 mg Naloxone HCl by IV Injection (Treatment A). Plasma samples analyzed using a bioanalytical method with a validated range of 0.0100 to 10.0 ng/mL; concentrations reported in ng/mL to 3 significant figures; concentrations below limit of quantification were set to zero (0.00 ng/mL) in the data summarization.

| Treatment | Time (h) | n | Mean (ng/mL) | SD (ng/mL) | Min (ng/mL) | Median (ng/mL) | Max (ng/mL) | CV % |
|---|---|---|---|---|---|---|---|---|
| A | 0.00 | 12 | 0.00 | 0.00 | 0.00 | 0.00 | 0.00 | NC |
| | 0.03 | 12 | 4.24 | 3.00 | 0.232 | 3.87 | 11.0 | 70.68 |
| | 0.08 | 12 | 2.26 | 0.876 | 1.45 | 1.99 | 4.39 | 38.79 |
| | 0.17 | 12 | 1.38 | 0.386 | 0.818 | 1.49 | 1.99 | 28.04 |
| | 0.25 | 12 | 1.11 | 0.406 | 0.574 | 1.04 | 1.95 | 36.53 |
| | 0.33 | 12 | 0.892 | 0.246 | 0.456 | 0.856 | 1.40 | 27.62 |
| | 0.42 | 12 | 0.747 | 0.202 | 0.445 | 0.722 | 1.19 | 26.99 |
| | 0.50 | 12 | 0.668 | 0.218 | 0.416 | 0.645 | 1.16 | 32.66 |
| | 0.75 | 12 | 0.521 | 0.155 | 0.351 | 0.496 | 0.880 | 29.78 |
| | 1.00 | 12 | 0.418 | 0.146 | 0.265 | 0.389 | 0.740 | 35.04 |
| | 2.00 | 12 | 0.255 | 0.0878 | 0.132 | 0.240 | 0.396 | 34.42 |
| | 4.00 | 12 | 0.0885 | 0.0434 | 0.0374 | 0.0747 | 0.174 | 49.11 |
| | 8.00 | 12 | 0.00647 | 0.00844 | 0.00 | 0.00 | 0.0220 | 130.36 |

NC = Not calculated

TABLE 7

Descriptive Statistics for Naloxone Concentration-Time Data after Administration of 1 mg Naloxone HCl by IM Injection (Treatment B). Plasma samples analyzed using a bioanalytical method with a validated range of 0.0100 to 10.0 ng/mL; concentrations reported in ng/mL to 3 significant figures; concentrations below limit of quantification were set to zero (0.00 ng/mL) in the data summarization.

| Treatment | Time (h) | n | Mean (ng/mL) | SD (ng/mL) | Min (ng/mL) | Median (ng/mL) | Max (ng/mL) | CV % |
|---|---|---|---|---|---|---|---|---|
| B | 0.00 | 12 | 0.00 | 0.00 | 0.00 | 0.00 | 0.00 | NC |
| | 0.03 | 11 | 0.595 | 0.773 | 0.00 | 0.190 | 2.35 | 129.80 |
| | 0.08 | 12 | 1.72 | 1.34 | 0.178 | 1.31 | 4.43 | 78.03 |
| | 0.17 | 12 | 1.99 | 1.05 | 0.362 | 1.93 | 3.99 | 52.74 |
| | 0.25 | 11 | 1.91 | 0.759 | 0.519 | 1.85 | 3.37 | 39.82 |
| | 0.33 | 12 | 1.97 | 0.871 | 0.540 | 1.74 | 3.48 | 44.13 |
| | 0.42 | 12 | 1.73 | 0.518 | 0.746 | 1.72 | 2.63 | 30.00 |
| | 0.50 | 12 | 1.67 | 0.568 | 0.764 | 1.75 | 2.72 | 33.93 |
| | 0.75 | 12 | 1.41 | 0.597 | 0.715 | 1.31 | 2.86 | 42.50 |
| | 1.00 | 12 | 1.07 | 0.340 | 0.617 | 1.00 | 1.66 | 31.73 |
| | 2.00 | 12 | 0.825 | 0.288 | 0.537 | 0.784 | 1.38 | 34.87 |

TABLE 7-continued

Descriptive Statistics for Naloxone Concentration-Time Data after Administration of 1 mg Naloxone HCl by IM Injection (Treatment B). Plasma samples analyzed using a bioanalytical method with a validated range of 0.0100 to 10.0 ng/mL; concentrations reported in ng/mL to 3 significant figures; concentrations below limit of quantification were set to zero (0.00 ng/mL) in the data summarization.

| Treatment | Time (h) | n | Mean (ng/mL) | SD (ng/mL) | Min (ng/mL) | Median (ng/mL) | Max (ng/mL) | CV % |
|---|---|---|---|---|---|---|---|---|
| | 4.00 | 12 | 0.406 | 0.165 | 0.125 | 0.404 | 0.695 | 40.64 |
| | 8.00 | 12 | 0.0470 | 0.0269 | 0.0145 | 0.0479 | 0.0922 | 57.25 |

NC = Not calculated

TABLE 8

Descriptive Statistics for Naloxone Concentration-Time Data after Administration of 1 mg Naloxone HCl by SC Injection (Treatment C). Plasma samples analyzed using a bioanalytical method with a validated range of 0.0100 to 10.0 ng/mL; concentrations reported in ng/mL to 3 significant figures; concentrations below limit of quantification were set to zero (0.00 ng/mL) in the data summarization.

| Treatment | Time (h) | n | Mean (ng/mL) | SD (ng/mL) | Min (ng/mL) | Median (ng/mL) | Max (ng/mL) | CV % |
|---|---|---|---|---|---|---|---|---|
| C | 0.00 | 12 | 0.00 | 0.00 | 0.00 | 0.00 | 0.00 | NC |
| | 0.03 | 12 | 0.426 | 0.603 | 0.00 | 0.177 | 2.02 | 141.55 |
| | 0.08 | 12 | 1.64 | 1.09 | 0.0556 | 1.54 | 3.14 | 66.63 |
| | 0.17 | 12 | 2.12 | 0.970 | 0.352 | 2.50 | 3.16 | 45.74 |
| | 0.25 | 12 | 1.84 | 0.713 | 0.541 | 2.06 | 2.65 | 38.69 |
| | 0.33 | 12 | 1.64 | 0.489 | 0.685 | 1.85 | 2.27 | 29.84 |
| | 0.42 | 12 | 1.56 | 0.329 | 0.983 | 1.67 | 2.10 | 21.10 |
| | 0.50 | 12 | 1.37 | 0.364 | 0.782 | 1.49 | 2.02 | 26.50 |
| | 0.75 | 12 | 1.12 | 0.274 | 0.652 | 1.05 | 1.68 | 24.56 |
| | 1.00 | 12 | 0.968 | 0.310 | 0.506 | 0.930 | 1.54 | 31.99 |
| | 2.00 | 12 | 0.718 | 0.214 | 0.318 | 0.711 | 1.01 | 29.82 |
| | 4.00 | 12 | 0.409 | 0.142 | 0.165 | 0.405 | 0.726 | 34.74 |
| | 8.00 | 12 | 0.0648 | 0.0486 | 0.0242 | 0.0461 | 0.176 | 75.04 |

NC = Not calculated

TABLE 9

Descriptive Statistics for Naloxone Concentration-Time Data after Intranasal Administration of 2 mg NNS (Treatment D). Plasma samples analyzed using a bioanalytical method with a validated range of 0.0100 to 10.0 ng/mL; concentrations reported in ng/mL to 3 significant figures; concentrations below limit of quantification were set to zero (0.00 ng/mL) in the data summarization.

| Treatment | Time (h) | n | Mean (ng/mL) | SD (ng/mL) | Min (ng/mL) | Median (ng/mL) | Max (ng/mL) | CV % |
|---|---|---|---|---|---|---|---|---|
| D | 0.00 | 11 | 0.00 | 0.00 | 0.00 | 0.00 | 0.00 | NC |
| | 0.03 | 12 | 0.0683 | 0.0804 | 0.00 | 0.0376 | 0.265 | 117.70 |
| | 0.08 | 12 | 0.607 | 0.653 | 0.0107 | 0.360 | 2.19 | 107.62 |
| | 0.17 | 12 | 1.17 | 1.05 | 0.0685 | 0.903 | 3.28 | 89.73 |
| | 0.25 | 12 | 1.44 | 1.02 | 0.133 | 1.14 | 3.07 | 70.86 |
| | 0.33 | 12 | 1.71 | 1.14 | 0.285 | 1.75 | 3.49 | 66.75 |
| | 0.42 | 12 | 1.70 | 1.03 | 0.393 | 1.77 | 3.32 | 60.49 |
| | 0.50 | 12 | 1.64 | 0.824 | 0.450 | 1.73 | 2.90 | 50.37 |
| | 0.75 | 12 | 1.22 | 0.381 | 0.533 | 1.28 | 1.94 | 31.35 |
| | 1.00 | 12 | 0.891 | 0.251 | 0.433 | 0.941 | 1.28 | 28.23 |
| | 2.00 | 12 | 0.464 | 0.128 | 0.308 | 0.418 | 0.656 | 27.63 |
| | 4.00 | 12 | 0.202 | 0.0827 | 0.128 | 0.176 | 0.372 | 40.89 |
| | 8.00 | 12 | 0.0301 | 0.0134 | 0.0125 | 0.0269 | 0.0565 | 44.44 |

NC = Not calculated

TABLE 10

Descriptive Statistics for Naloxone Concentration-Time Data after Intranasal Administration of 1 mg NNS (Treatment E). Plasma samples analyzed using a bioanalytical method with a validated range of 0.0100 to 10.0 ng/mL; concentrations reported in ng/mL to 3 significant figures; concentrations below limit of quantification were set to zero (0.00 ng/mL) in the data summarization.

| Treatment | Time (h) | n | Mean (ng/mL) | SD (ng/mL) | Min (ng/mL) | Median (ng/mL) | Max (ng/mL) | CV % |
|---|---|---|---|---|---|---|---|---|
| E | 0.00 | 15 | 0.00 | 0.00 | 0.00 | 0.00 | 0.00 | NC |
|   | 0.03 | 15 | 0.0144 | 0.0266 | 0.00 | 0.00 | 0.0748 | 185.18 |
|   | 0.08 | 15 | 0.142 | 0.220 | 0.00 | 0.0709 | 0.891 | 154.72 |
|   | 0.17 | 15 | 0.392 | 0.464 | 0.0172 | 0.288 | 1.91 | 118.25 |
|   | 0.25 | 14 | 0.616 | 0.525 | 0.0361 | 0.501 | 2.04 | 85.17 |
|   | 0.33 | 14 | 0.652 | 0.412 | 0.0581 | 0.704 | 1.39 | 63.18 |
|   | 0.42 | 14 | 0.736 | 0.408 | 0.0867 | 0.810 | 1.42 | 55.44 |
|   | 0.50 | 15 | 0.708 | 0.422 | 0.114 | 0.691 | 1.70 | 59.65 |
|   | 0.75 | 15 | 0.567 | 0.231 | 0.155 | 0.567 | 0.986 | 40.71 |
|   | 1.00 | 15 | 0.471 | 0.197 | 0.156 | 0.460 | 0.882 | 41.86 |
|   | 2.00 | 15 | 0.242 | 0.0776 | 0.137 | 0.226 | 0.423 | 32.09 |
|   | 4.00 | 15 | 0.0960 | 0.0446 | 0.0391 | 0.0912 | 0.195 | 46.48 |
|   | 8.00 | 15 | 0.0139 | 0.0107 | 0.00 | 0.0133 | 0.0314 | 76.47 |

NC = Not calculated

TABLE 11

Descriptive Statistics for Naloxone Concentration-Time Data after IN/MAD Administration of 2 mg/2 mL Naloxone HCl (Treatment F). Plasma samples analyzed using a bioanalytical method with a validated range of 0.0100 to 10.0 ng/mL; concentrations reported in ng/mL to 3 significant figures; concentrations below limit of quantification were set to zero (0.00 ng/mL) in the data summarization

| Treatment | Time (h) | n | Mean (ng/mL) | SD (ng/mL) | Min (ng/mL) | Median (ng/mL) | Max (ng/mL) | CV % |
|---|---|---|---|---|---|---|---|---|
| F | 0.00 | 7 | 0.00 | 0.00 | 0.00 | 0.00 | 0.00 | NC |
|   | 0.03 | 6 | 0.00324 | 0.00794 | 0.00 | 0.00 | 0.0194 | 244.95 |
|   | 0.08 | 7 | 0.159 | 0.120 | 0.0356 | 0.151 | 0.357 | 75.38 |
|   | 0.17 | 7 | 0.455 | 0.163 | 0.205 | 0.462 | 0.745 | 35.76 |
|   | 0.25 | 6 | 0.505 | 0.214 | 0.273 | 0.487 | 0.779 | 42.43 |
|   | 0.33 | 6 | 0.445 | 0.151 | 0.218 | 0.485 | 0.628 | 33.98 |
|   | 0.42 | 7 | 0.433 | 0.147 | 0.209 | 0.417 | 0.670 | 33.98 |
|   | 0.50 | 6 | 0.391 | 0.116 | 0.234 | 0.396 | 0.523 | 29.52 |
|   | 0.75 | 7 | 0.315 | 0.0766 | 0.206 | 0.307 | 0.417 | 24.30 |
|   | 1.00 | 7 | 0.266 | 0.0561 | 0.202 | 0.258 | 0.363 | 21.13 |
|   | 2.00 | 7 | 0.160 | 0.0400 | 0.0982 | 0.154 | 0.215 | 25.00 |
|   | 4.00 | 7 | 0.0605 | 0.0184 | 0.0364 | 0.0569 | 0.0870 | 30.47 |
|   | 8.00 | 7 | 0.0112 | 0.00515 | 0.00 | 0.0127 | 0.0158 | 45.94 |

NC = Not calculated

Discussion of Results

IV administration of 0.4 mg naloxone produced rapid achievement of the highest blood levels observed in the trial overall. Due to rapid redistribution and clearance, blood levels declined quickly and were below values achieved after IM, SC and NNS in 20-30 minutes. IM and SC administration of 1 mg naloxone demonstrated a typical absorption phase that peaked in 10-20 minutes, with IM administration having a longer time to maximum concentration as compared to SC. Blood levels remained sustained for 20-30 minutes and then declined. IM and SC total exposures were roughly equivalent.

Naloxone nasal spray 2 mg produced a concentration-time curve and total exposure that compares favorably to the IM and SC exposure. A maximum concentration of 2 ng/mL was achieved, which is roughly 80% of that achieved after IM and SC administration of 1 mg naloxone. Total exposure is comparable, at about 75% of the AUC. The median time to reach maximum concentration was 24 minutes versus 20 and 10 minutes for IM and SC, respectively. These are not considered to be clinically meaningful differences in time to reach maximum concentration. Naloxone nasal spray 1 mg had parameters that were roughly dose proportionate to naloxone nasal spray 2 mg.

Arm F represents the current off-label medical practice of administering 2 mg naloxone injection intranasally using the 510(k)-cleared Mucosal Atomization Device (MAD™ Nasal). The data are quite striking in that the maximum plasma level and total exposure are roughly 20-25% of IM and SC 1 mg values. Arm D, naloxone nasal spray 2 mg, produces a relative exposure three to four times that of Arm F.

An ANOVA table (Table 7) is provided which explains the comparison of log-transformed AUC and $C_{max}$ comparison of Arm D, 2 mg naloxone nasal spray, to the relevant approved routes of administration. Arms B and C were analyzed using the administered 1 mg doses. The ratios of test and reference suggest that 1 mg IM and SC produce a percent ratio of about 140% for AUC and $C_{max}$ at these doses.

Using the pilot data, the IM route appears to be most comparable to the naloxone nasal spray with regard to rate and extent of absorption. The time to maximum concentration is 20 versus 24 minutes for IM and naloxone nasal spray, respectively. Moreover, the IM dose can be reduced from 1 mg used in this pilot study, to 0.4 mg (lowest labeled dose). The maximum and total exposure from IM administration is likely to drop by half based on the studies set forth above, and the naloxone nasal spray will clearly have exposure superior to the 0.4 mg IM dose, the lowest FDA approved dose.

The most common complaint from the nasal spray by the subjects was that it tasted bad, which is common with nasal sprays. No subject had any findings of nasal mucosal damage after inspection of the nasal cavity by an otolaryngologist. The formulation was well tolerated and non toxic to the subjects.

CONCLUSIONS

The pilot study accomplished its stated goals of understanding naloxone nasal spray plasma level exposure compared to other doses and routes of administration. The relative local toxicity of 1 and 2 mg naloxone nasal spray (10 mg/mL) is now described. The exposure and relative tolerability of 2 mg naloxone injection (1 mg/mL) administered nasally is also now understood.

The pilot study results suggest that exposure after SC injection is very similar to IM injection. The pilot study dose was slightly higher (1 mg) than the 0.8 mg dose reported in Dowling, and shows roughly proportionate increases in $C_{max}$ and AUC. Naloxone is a very water-soluble drug, and thus, one could reasonably expect a dose proportional decrease in systemic exposure in the 1 mg IM and SC doses in the pilot study, and the 0.8 mg dose in Dowling. Approved naloxone injection is labeled for a dose range of 0.4 mg and higher to be administered IV, IM, or SC. A 0.4 mg dose given by IM or SC injection would yield a Cmax of roughly 1 ng/mL. A 1 ng/mL Cmax value would thus be estimated to be the lowest Cmax achieved using an approved dose and route of administration. Although the current clinically-used 2 mg dose administered by IN/MAD only resulted in a naloxone Cmax of 0.5 ng/mL.

Next, Applicant surprisingly discovered superior bioavailability of nasal naloxone spray, as compared to naloxone nasal spray from Dowling and nasal spray administered with a MAD device.

Total exposure estimates (AUC) can be considered similarly to Cmax as a measure of bioavailability. Reduction of total exposure secondary to reducing the IM dose from 1 mg to 0.4 mg will result in Arm D having a significantly greater total exposure than a 0.4 mg IM injection. Plasma levels (0-2 hours) are shown in FIG. 1.

Naloxone 1301 Study Synopsis

This is an open-label, single-dose, random treatment sequence, 3-period crossover, single-center study which enrolled 36 randomized healthy male and female volunteers.

TABLE 11A

| naloxone1301 Treatment | Dose: Naloxone HCl |
|---|---|
| Treatment A | 2 mg intranasal naloxone HCl solution using 2 sprays of 10 mg/mL naloxone HCl (1 spray [1 mg/100 µL] in each nostril) |
| Treatment B | 2 mg + 2 mg in five minutes intranasal naloxone HCl solution using 2 sprays of 10 mg/mL naloxone HCl (1 spray [1 mg/100 µL] in each nostril, repeated once at a five minute interval) |
| Treatment C | 0.4 mg/1 mL commercially available naloxone HCl injection administered by intramuscular injection |

Treatments A and C are of primary interest for pharmacokinetic and statistical analysis. Treatment C was chosen as the reference treatment after review of the pilot study data. The dose of 0.4 mg is the lowest labeled dose of naloxone injection. The time to maximum concentrations observed in study naloxone 1201 were 0.33 and 0.42 hours, or 20 and 24 minutes, respectfully, for 1 mg IM and 2 mg naloxone nasal spray. Given the pilot data outcomes, the peak and total exposure of 2 mg naloxone nasal spray was expected to be considerably higher than 0.4 mg IM naloxone, perhaps as much as twofold.

Treatment B will provide useful information since naloxone is a drug that is titrated to clinical effect if the initial dose is insufficient. Therefore, Treatment B, which includes re-dosing was added which will increase exposure after a short period, 5 minutes from initial dosing, and mirrors clinical practice with naloxone injection. The nominal sample collection times for Treatment B were related to the first dose (first 2 sprays) in be consistent with the collection times recorded for Treatment A. This re-administration treatment will also provide safety data supporting re-dosing.

Unconjugated (free) naloxone was determined by the same validated LC/MS/MS bioanalytical assay method that was used for the naloxone 1201 study.

Non-compartmental pharmacokinetic analysis was performed in Phoenix™ WinNonlin® (Version 6.3, Pharsight Corporation) to analyze plasma concentration-time data using nominal sample collection times.

Pharmacokinetic Results

Table 11B lists the pharmacokinetic parameters determined for free naloxone. Median $t_{max}$ was 0.167 hours (10 minutes) following IM administration while median $t_{max}$ for intranasal administration was 0.333 hours (20 minutes) for the 2 mg dose and 0.417 hours (25 minutes) for the 2 mg+2 mg dose where the doses were separated by 5 minutes. Although $t_{max}$ occurred slightly later following intranasal administration compared to IM administration, intranasal administration resulted in higher exposure (both $C_{max}$ and $AUC_{0-inf}$) compared to IM administration. Mean $t_{1/2}$ was not affected by the route of administration or the total dose and was similar across the three treatments.

TABLE 11B

PK Parameters from Study naloxone 1301

| Treatment | Statistic | $t_{max}$[a] (h) | $C_{max}$ (ng/mL) | $AUC_{0-inf}$ (ng * h/ mL) | $t_{1/2}$ (h) |
|---|---|---|---|---|---|
| Treatment A | N | 33 | 33 | 33 | 33 |
| (2 mg IN) | Mean | 0.333 | 1.78 | 2.63 | 1.37 |
| | SD | — | 0.967 | 1.27 | 0.339 |
| | Min | 0.250 | 0.564 | 1.22 | 0.926 |
| | Max | 0.750 | 4.43 | 5.62 | 2.53 |
| Treatment B | N | 35 | 35 | 35 | 35 |
| (2 mg + 2 mg IN) | Mean | 0.417 | 3.06 | 4.42 | 1.41 |
| | SD | — | 1.63 | 2.19 | 0.324 |
| | Min | 0.167 | 1.12 | 2.05 | 0.833 |
| | Max | 1.00 | 8.75 | 10.9 | 2.06 |
| Treatment C | N | 34 | 34 | 34 | 34 |
| (0.4 mg IM) | Mean | 0.167 | 1.05 | 1.67 | 1.38 |
| | SD | — | 0.353 | 0.363 | 0.274 |
| | Min | 0.083 | 0.343 | 1.10 | 0.876 |
| | Max | 1.00 | 1.78 | 3.05 | 2.11 |

[a] median rather than mean is presented for this parameter.

Example 4

Stability of Naloxone HCl in 25 mM Citrate Buffer at pH 3.0, 4.0, and 5.0

Formulations of naloxone HCl (20 mg/mL) were formulated at different pH values (3-5) in citrate buffer and then stored at accelerated conditions (60° C.) or exposed to light. Based on the results, all formulations were characterized for pH and osmolarity according to specific standard operating procedures at the beginning of the experiment and at the end to monitor any changes.

A stock solution of citric acid buffer (25 mM) was prepared at pH 3, 4 and 5 using dilute sodium hydroxide to adjust the pH. Naloxone HCl (20 mg) was added to a 1-mL aliquot the buffer at each pH to make a 0.5 mg/mL naloxone HCl solution. After adding naloxone HCl, no further pH adjustments were made. Samples were analyzed for pH and Osmolarity at Day 0 and Day 15 and by RP-HPLC for Naloxone-HCl at Day 15.

The pH of the formulations remained relatively constant throughout the 15 day study. In all conditions, pH 5 showed the most degradation with the largest increase in peak area at RRT 0.52. The degradant at RRT 1.16 appears to be less stable at lower pH values. A summary of pH, osmolarity and appearance results are summarized in the following Table 12.

TABLE 12 pH, Osmolarity, and Appearance Results for Formulations, Day 15

| | Formulation | pH | Osmolarity (mOsm) | Appearance |
|---|---|---|---|---|
| INITIAL RESULTS | Naloxone HCl 0.5 mg/mL Control | 4.06 | 85, 85, 83 | Clear colorless solution |
| | Naloxone HCl 0.5 mg/mL in Citrate Buffer (pH 3) | 2.88 | 119, 118, 119 | Clear colorless solution |
| | Naloxone HCl 0.5 mg/mL in Citrate Buffer (pH 4) | 3.88 | 130, 129, 131 | Clear colorless solution |
| | Naloxone HCl 0.5 mg/mL in Citrate Buffer (pH 5) | 4.91 | 139, 140, 140 | Clear colorless solution |
| | Citrate Buffer Blank (pH 4) | 4.03 | 43, 43, 43 | Clear colorless solution |
| 60° C. | Naloxone HCl 0.5 mg/mL Control | 4.29 | 140, 142 | clear colorless solution |
| | Naloxone HCl 0.5 mg/mL in Citrate Buffer (pH 3) | 2.85 | 133 | Very slight tint of yellow clear solution |
| | Naloxone HCl 0.5 mg/mL in Citrate Buffer (pH 4) | 3.90 | 165 | Very slight tint of yellow clear solution |
| | Naloxone HCl 0.5 mg/mL in Citrate Buffer (pH 5) | 4.77 | 156 | Very slight tint of yellow clear solution |
| | Citrate Buffer Blank (pH 4) | 3.65 | 65 | clear colorless solution |

Figure 3:
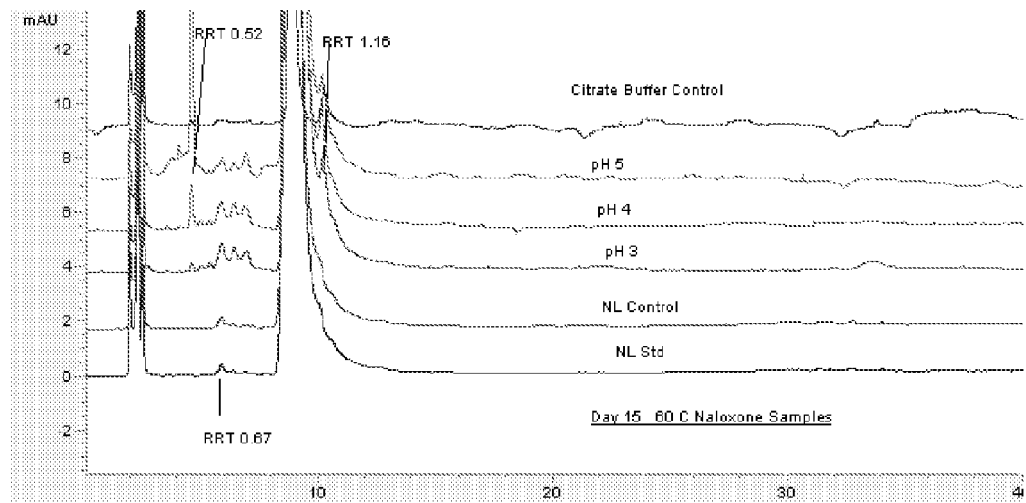
FIG. 3 is a graph depicting stability of naloxone samples of varying formulations at 60° C.

Degradation was observed with samples stored at 60° C. for 15 days (See FIG. 3). Degradants with a relative retention times (RRT) of 0.52 and 1.2 were seen under all conditions.

Example 5

Evaluation of Excipients in Naloxone HCl Formulations

A number of excipients including buffers, preservatives, oxidants, and viscosity enhancers for compatibility, were evaluated with Naloxone at a concentration of 20 mg/mL. Thirteen excipient combinations were evaluated in preliminary formulation screening studies. The composition of the thirteen 20 mg/mL formulations is summarized in the following Table 13. The formulations were at pH 5.0, to accelerate degradation, unless otherwise noted in the following Table 13. Each formulation was stored at 60° C. for 4 weeks in sealed 5 mL vials with 1 mL fill volumes. Analysis included osmolality, pH, and a Naloxone RP-HPLC assay for purity.

TABLE 13

Preliminary Formulation Screening Studies

| | Formulation No. | | | | | | | | | | | | |
|---|---|---|---|---|---|---|---|---|---|---|---|---|---|
| | 4 | 5 | 6 | 7 | 8 | 9 | 10 | 11 (pH 4.0) | 12 | 13 | 13A (pH 4.5) | 14 | 14A (pH 4.5) |
| Citric Acid (25 mM) | x | x | x | x | | | | | | | | | |
| Citric Acid (2.0 mg/mL) | | | | | | | | x | | x | x | | x |
| Sodium Citrate (3.1 mg/mL) | | | | | | | | x | | x | x | | x |
| EDTA (10 mM) | x | x | x | | x | x | | x | | x | x | | x |
| Ascorbic Acid (10 mM) | x | x | | | | | | | | | | | |
| Hypromellose (0.1%) | | | x | | x | x | x | | | | | | |
| Polyethylene Glycol 400 (20%) | | | | | x | | | | | | | | |
| Sorbitol (5%) | | | x | x | | | x | | | | | | |
| Glycerine (2.0%) | | | x | | | | | | | x | x | x | x |
| Propylene Glycol (1.0%) | | | | | | | | | x | x | x | x | |
| Methylparaben (1.8 mg/mL) | | x | x | x | | | | | | | | | |
| Propylparaben (0.2 mg/mL) | | x | x | x | | | | | | | | | |
| Benzalkonium Chloride (0.125%) | x | x | | | | | x | | | | x | x | |
| Benzyl Alcohol (0.5%) | | | | | | | | | x | x | | | |
| Sodium Chloride (6.4 mg/mL) | x | x | x | | | | | | | x | x | x | x |
| Polysorbate 20 (0.02%) | | | | | | | | | x | x | x | x | |
| Nitrogen Gas | x | x | x | x | x | x | x | x | x | x | x | x | x |

*Formulation was examined at three different pH values and at two storage conditions for a total of six different formulations (FIGS. 1 and 2).
**Nitrogen gas will be sparged in the bulk solution in addition to a nitrogen overlay. All other formulations with nitrogen will be an overlay.

Earlier experiments examined the effects of pH and storage conditions (accelerated by elevated temperature) on the stability of naloxone HCl. Increasing the pH of the solution accelerated the degradation of naloxone HCl resulting in the formation of a major degradant at a relative retention time (RRT) of 0.52. However, it was found that decreasing the pH minimizes the formation of potential oxidative degradants. Based on these results, it has been discovered that a slightly acidic pH and buffer excipients or manufacturing controls, will optimize the formulation to prevent any hydrolysis or oxidative degradation and keep pH in range suitable for comfortable nasal administration. The results further surprisingly showed that the use of benzalkonium chloride, a common nasal product preservative, resulted in an additional degradant in formulations 7, 9, 14, and 14A. Apart from the preservative, Formulation 7 was believed to be ideal for nasal delivery because the excipients were expected to increase the residence time in the nasal cavity (HPMC), prevent oxidation (EDTA), and create a hyperosmotic solution that facilitates diffusion across the cell membrane.

This screening study indicated the following: the formulation should be buffered and a citric acid based buffer system was acceptable and disodium EDTA did not adversely impact Naloxone in formulations. In this initial study, the preliminary conclusion was that benzyl alcohol and paraben preservatives were acceptable, but benzalkonium chloride was not, due to increased observed degradation. Ascorbic acid was also not acceptable due to increased observed degradation. From the screening study, four combinations of excipients were selected for further formulation development. These excipients included Citric Acid, EDTA, NaCl, Benzyl Alcohol, methylparaben, propyl paraben, sorbitol, glycerine, hypromellose, and propylene glycol. However, later studies indicated that common preservatives methyl paraben and propylene glycol and glycerine were found to relatively negatively impact the formulation, in particular these agents caused increased naloxone degradation and increased impurities as analyzed by HPLC, compared to other formulation compositions.

Permeability and viscocity enhancer, including sorbitol, hypromellose, propylene glycol and glycerine, were believed to be necessary for the product have increased residence time in the nasal cavity, however, it was found that these excipients caused an increase in degradation under stress conditions (temperature and oxygen exposure).

Further, it was found that formulations having a combination of EDTA, hypromellose, methylparaben, and propylparaben, exhibited poor solubility such that a suitable solution could not be obtained. Viscosity/permeability enhancers commonly used in nasal formulations (at concentrations used in Table 13) such as hypromellose, polyethylene glycol 400, sorbitol, glycerine, and polypropylene glycol, were also assessed and determined to be unsuitable in the formulations due to increased degradation of naloxone and/or decreased suitability for nasal spray actuation.

Net, Applicant found that, surprisingly, commonly used excipients including one or more ascorbic acid, hypromellose, propylene glycol 400, sorbitol, glycerine, polypropylene glycol, methylparaben, propylparaben, benzylalkonium chloride, were found to increase degradation of naloxone. While some of the excipients might work individually, the combination of many of these was found to be unacceptable for various reasons as outlined above. Equally surprising was that the disclosed compositions, which lack commonly used excipients and combinations of commonly used excipients, had superior stability as compared to more complex formulations and remained stable for a period of up to 36 months under ambient conditions.

Example 6

Formulation Modifications

Four formulations were chosen from the 13 formulations in the preliminary study, described in the example above, for further analysis under these stress conditions with some modifications. The formulations were designated 4M, 7M, 8M, and 13M. The composition of these revised 20 mg/mL Naloxone HCl formulations is summarized below in the following Table 14. One mL of each formulation was filled into 5 mL vials. Accelerated stability storage conditions were designed to maximize degradation, specifically elevated pH, 5.0, filled in a glove box with an oxygen rich environment, and 60° C. storage temperature.

TABLE 14

Compositions of Modified Formulations 4M, 7M, 8M, and 13M

| Formulation No. | 4M | 7M | 8M | 13M |
|---|---|---|---|---|
| Citric Acid (25 mM) | x | x | x | |
| Citric Acid (2.0 mg/mL) | | | | x |
| Sodium Citrate (3.1 mg/mL) | | | | x |
| EDTA (10 mM) | x | x | x | x |
| Hypromellose (0.1%) | | x | | |
| Sorbitol (5%) | | x | | |
| Glycerine (1.0%) | | | | x |
| Propylene Glycol (0.5%) | | | | x |
| Methylparaben (1.8 mg/mL) | | | x | |
| Propylparaben (0.2 mg/mL) | | | x | |
| Benzyl Alcohol (0.5%) | x | x | | x |

Results for the 12 week study are summarized in the following Table 15 for changes in pH, osmolality, and total % of impurities by the Ph Eur Related Substances HPLC method

TABLE 15

Accelerated Stability Results for Formulations 4M, 7M, 8M and 13M

| Formulation # | pH | | Osmolality (mOsm) | | Total Impurities by HPLC | |
|---|---|---|---|---|---|---|
| | Beginning of Study | End of Study | Beginning of Study | End of Study | Beginning of Study | End of Study |
| 4M | 4.96 | 4.93 | 173 | 179 | 0.47 | 3.64 |
| 7M | 4.73 | 4.73 | 609 | 616 | 0.25 | 3.57 |
| 8M | 4.91 | 4.26 | 301 | 301 | 0.22 | 6.85 |
| 13M | 4.99 | 4.82 | 1170 | 1166 | 0.21 | 5.75 |

Based on these results from this 12 week accelerated stability study, Formulations 4M and 7M were selected for a four week accelerated stability study. Formulations 8M and 13M were eliminated due relatively higher degradation under accelerated conditions. Surprisingly, the parabens in formulations 8M resulted in greater degradation as compared to the formulation 4M that used benzyl alcohol as a preservative in an essentially equivalent formulation, as evidenced by the doubling of total impurities as measured by HPLC.

Example 7

Stability Results for Formulations 4M and 7M, Nitrogen and Oxygen Overlay

The final formulation selection study compared stability of 20 mg/mL Naloxone HCl in modified Formulations 4M and 7M with nitrogen and oxygen overlays. 1 mL of each formulation was placed in a 5 mL stoppered vial and stored at 60° C. for 4 weeks. The following Table 16 shows total impurities generated over time at 60° C. with nitrogen and oxygen overlays for Formulas 4M and 7M. (See also FIG. 3.)

TABLE 16

Total impurities area % with nitrogen overlay and oxygen overlay at 60° C.

| Stability Condition | Formulation | 0 Days | 3 Days | 7 Days | 14 Days | 28 days |
|---|---|---|---|---|---|---|
| $N_2$ Overlay, 60° C. | 4M | 0.09 | 0.24 | 0.059 | 0.93 | 1.61 |
| | 7M | 0.08 | 0.35 | 0.88 | 1.14 | 2.14 |
| $O_2$ Overlay, 60° C. | 4M | 0.09 | 0.28 | 0.34 | 1.09 | 1.7 |
| | 7M | 0.09 | 0.31 | 0.99 | 2.15 | 4.09 |

Formulation 4 showed no difference in degradants regardless of vial overlay conditions, in contrast to Formulation 7M which had markedly increased degradation with the oxygen overlay, evidencing the markedly improved stability of Formulation 4M in the presence of oxygen, as compared to Formulation 7M, having hypromellose and sorbitol. Osmolarity and pH were essentially unchanged over the course of the 4 week study.

Stability Results on Final Formulation

Figure 4A:
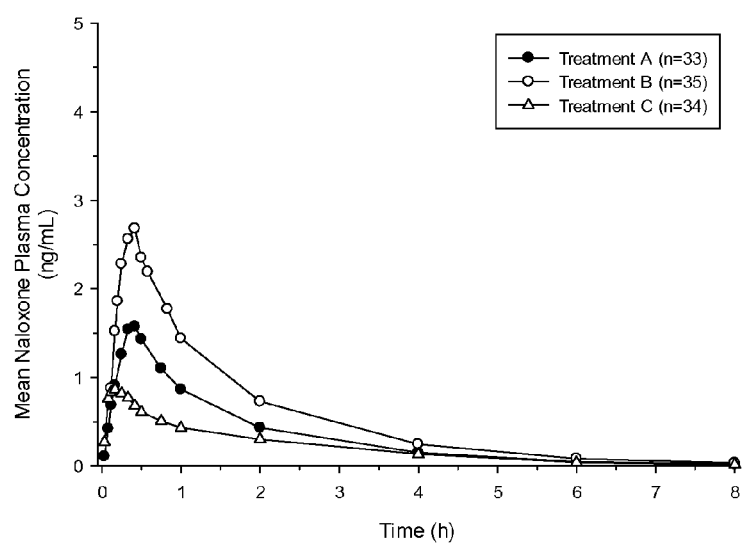
FIG. 4A depicts Mean Naloxone Plasma Concentration-time Profiles (0-8 hours), linear scale. Treatment A: 2 mg NNS; Treatment B: 2 mg+2 mg NNS; Treatment C: 0.4 mg naloxone IM
Figure 4B:
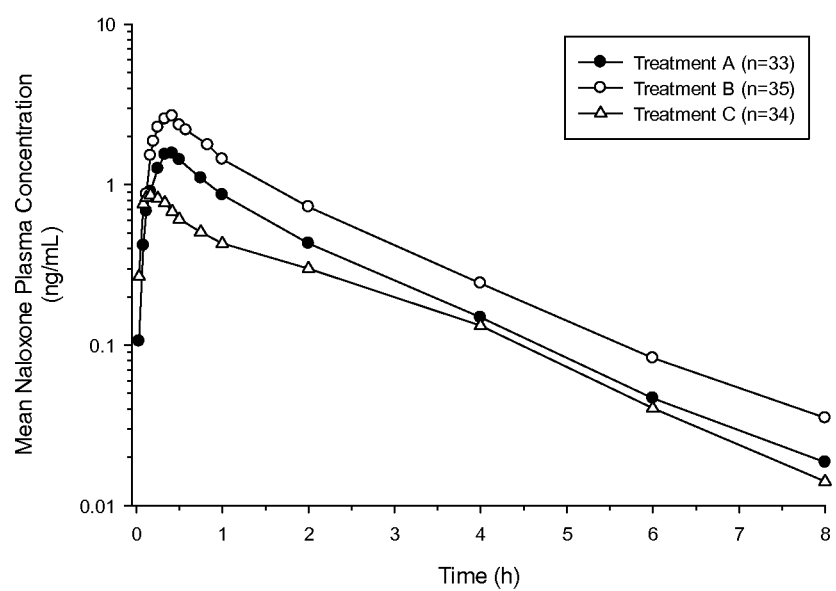
FIG. 4B depicts Mean Naloxone Plasma Concentration-time Profiles (0-8 hours), semi-logarithmic scale. Treatment A: 2 mg NNS; Treatment B: 2 mg+2 mg NNS; Treatment C: 0.4 mg naloxone IM
Figure 5:
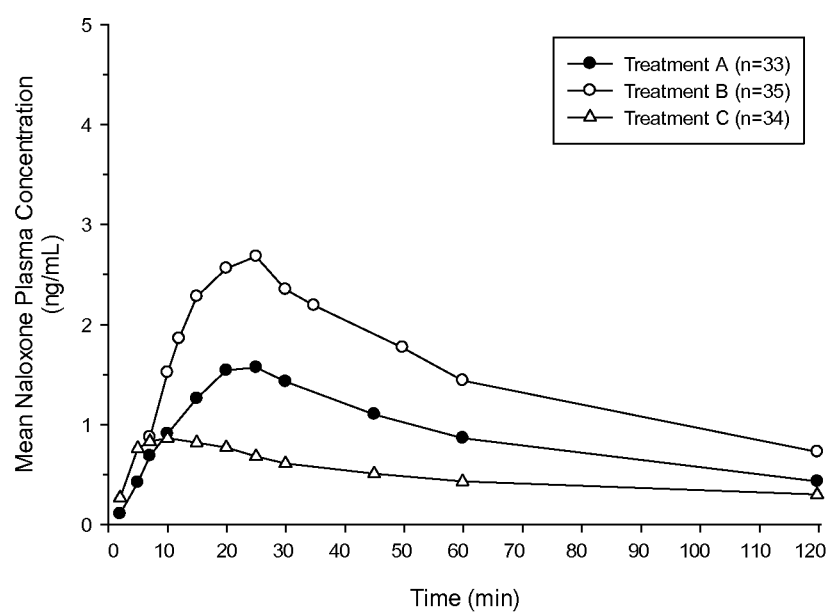
FIG. 5 depicts Mean Naloxone Plasma Concentration-time Profiles (0-120 minutes). Treatment A: 2 mg NNS; Treatment B: 2 mg+2 mg NNS; Treatment C: 0.4 mg naloxone IM.

Two batches of Naloxone Nasal Spray have been produced and placed on stability, Batch 200228 and 200274. The European Pharmacopoeia naloxone hydrochloride dihydrate monograph method and standards (RP-HPLC) were used to characterize the chemical stability of the batches. FIG. 4 shows that total impurities peak area percentage for each batch, including Naloxone Related Substances for each batch stored at 25° C./60% RH and 40° C./75% RH for 12 months. Degradation rate appears to taper off after 6 months. No 7,8 didehydronaloxone was detected after production and testing of the NNS. Table 17 lists the areas for impurities after 6 months of storage at 40° C./75% RH for each batch with product stored upright and downward. Product in the downward position is in contact with the stopper, such that the potential effects of the stopper on degradation can be determined. ND=not detected. <LOQ=less than limit of quantitation.

TABLE 17

Area Percentage of Impurities in Naloxone Nasal Spray after 6 Months at 40° C./75% RH.

| | Batch 200228 | | Batch 200274 | |
|---|---|---|---|---|
| | Up | Down | Up | Down |
| Naloxone Related Substance | | | | |
| 10-α-hydroxynaloxone | <LOQ | <LOQ | ND | ND |
| Oxymorphone | ND | ND | ND | ND |
| Noroxymorphone | <LOQ | <LOQ | ND | ND |
| 10-β-hydroxynaloxone | ND | ND | ND | ND |
| 7,8-didehydronaloxone | <LOQ | <LOQ | ND | ND |
| 2,2'-bisnaloxone | ND | <LOQ | ND | ND |
| 3-O-allylnlnaloxone | ND | ND | ND | ND |
| Unknown Impurities | | | | |
| RRT 0.348-0.349 | ND | ND | ND | ND |
| RRT 0.0547 | <LOQ | <LOQ | ND | ND |
| RRT 0.650-0.651 | .09% | .09% | 0.10 | 0.11% |
| RRT 0.718-0.724 | 0.52% | 0.52% | 0.80 | 0.75% |
| RRT 1.074-1.080 | <LOQ | <LOQ | ND | ND |
| RRT 2.776-2.780 | ND | ND | ND | ND |

All percentages, parts and ratios as used herein are by weight of the total composition, unless otherwise specified. All such weights as they pertain to listed ingredients are based on the active level and, therefore, do not include solvents or by-products that may be included in commercially available materials, unless otherwise specified. All numerical ranges as used herein, whether or not expressly preceded by the term "about," are intended and understood to be preceded by that term, unless otherwise specified.

Numerical ranges as used herein are intended to include every number and subset of numbers contained within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present invention shall include the corresponding plural characteristic or limitation, and vice versa, unless otherwise specified or clearly implied to the contrary by the context in which the reference is made.

All documents (patents, patent applications and other publications) cited in this application are incorporated herein by reference in their entirety.

What is claimed is:

1. A method of treating a known or suspected opioid overdose comprising the step of intranasally administering a composition comprising from about 5 mg/mL to about 50 mg/mL of an opioid antagonist naloxone; from about 5 mM to about 50 mM citric acid; from about 2 to about 20 mM disodium ethylene diamine tetraacetic acid (EDTA); from about 0.1 to about 2 weight % benzyl alcohol; and a carrier to an individual in need thereof,
    wherein said composition is administered via the nasal membranes to said individual;
    wherein said individual is administered a dose, per naris, of from about 0.1 to about 2 mg.

2. The method of claim 1, wherein said known or suspected opioid overdose is manifested by respiratory and/or central nervous system depression.

3. The method of claim 1, wherein said intranasal administration results in a $T_{max}$ of about 5 to about 30 minutes.

4. The method of claim 1, wherein said method utilizes a device having a property selected from needle-free, ready-to-use, disposable, or a combination thereof.

5. The method of claim 1, wherein said administration step comprises intranasal administration of a single spray per naris, wherein said spray may be repeated as necessary.

6. The method of claim 1, wherein administration of said composition intranasally results in a parameter selected from a $T_{max}$ of about 0.1 hours to about 0.5 hours in a subject; a peak plasma concentration of from about 1.0 to about 4.0 ng/mL at a time period of from about 5 to about 30 minutes after administration; and combinations thereof.

7. The method of claim 1, wherein said composition comprises
    a) about 10 mg/mL naloxone HCl dihydrate;
    b) about 25 mM citric acid;
    c) about 10 mM EDTA;
    d) about 0.5 weight % benzyl alcohol; and
    e) a pharmaceutically acceptable carrier;
    wherein intransal administration of about 200 μL of said composition achieves one or more parameters selected from a plasma concentration of about 1 ng/mL within about 5 to 15 minutes after intranasal administration; a $T_{max}$ of about 0.1 hours to about 0.5 hours, or about 0.3 hours; an $AUC_{0-inf}$ of from about 2.5 to about 4.5 ng–hr/mL, or about 2.5 to about 2.7 ng–hr/mL, or about 2.6 ng–hr/mL; and a Cmax of from about 1 to about 3 or about 1.5 to about 2.5 or about 1.8 ng/mL.

8. The method of claim 1, wherein said composition comprises
    a) about 7 mg/mL to about 11 mg/mL naloxone;
    b) about 20 mM to about 30 mM citric acid;
    c) about 5 mM to about 15 mM ethylenediaminetetraacetic acid; and
    d) about 0.2% to about 1.0 weight % benzyl alcohol;
    wherein the nasal spray has a pH of about 4.25±0.1.

9. The method of claim 1, wherein said composition comprises from about 5 mg/mL to about 50 mg/mL of naloxone;
    a) from about 5 mM to about 50 mM citric acid;
    b) from about 2 to about 20 mM disodium ethylene diamine tetraacetic acid (EDTA);

c) from about 0.1 to about 2 weight % benzyl alcohol; and
d) a carrier;
wherein said composition has a pH of about 4; and
wherein said composition has an osmolality of from about 300 to about 500 mOsm.

10. The method of claim 1, wherein said composition comprises naloxone hydrochloride dihydrate.

\* \* \* \* \*